(12) United States Patent
Masaki et al.

(10) Patent No.: US 12,372,773 B2
(45) Date of Patent: Jul. 29, 2025

(54) ENDOSCOPE ILLUMINATION LIGHT SWITCHING DEVICE AND ENDOSCOPE ILLUMINATION LIGHT SWITCHING METHOD

(71) Applicant: OLYMPUS CORPORATION, Tokyo (JP)

(72) Inventors: Takahiro Masaki, Shirakawa (JP); Yusuke Yoshida, Hachioji (JP); Takeshi Ito, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 1054 days.

(21) Appl. No.: 17/234,962

(22) Filed: Apr. 20, 2021

(65) Prior Publication Data
US 2021/0239965 A1 Aug. 5, 2021

Related U.S. Application Data

(63) Continuation of application No. PCT/JP2018/039395, filed on Oct. 23, 2018.

(51) Int. Cl.
*G02B 21/06* (2006.01)
*A61B 1/00* (2006.01)
(Continued)

(52) U.S. Cl.
CPC ........ *G02B 23/2461* (2013.01); *A61B 1/0016* (2013.01); *A61B 1/0646* (2013.01); *A61B 1/0684* (2013.01)

(58) Field of Classification Search
CPC ............... G02B 21/00; G02B 21/0004; G02B 21/0008; G02B 21/0012; G02B 21/0016;
(Continued)

(56) References Cited

U.S. PATENT DOCUMENTS 4,653,878 A * 3/1987 Nakasato ............... G02B 21/26
359/392
4,713,683 A * 12/1987 Fujimori .............. A61B 1/0655
348/E9.002
(Continued)

FOREIGN PATENT DOCUMENTS

EP 1752083 A1 2/2007
EP 2581033 A1 4/2013
(Continued)

OTHER PUBLICATIONS

International Search Report dated Jan. 22, 2019 issued in PCT/JP2018/039395.

*Primary Examiner* — Thong Q Nguyen
(74) *Attorney, Agent, or Firm* — Scully, Scott, Murphy & Presser, P.C.

(57) ABSTRACT

An endoscope illumination light switching device includes a rotation body in which a plurality of holes including a first hole are formed in a circumferential direction and that switches a hole on an irradiation optical path through rotation, a drive device configured to rotationally drive the rotation body, a sensor, and a processor configured to control a stop position of the rotation body based on a detection signal from the sensor. The rotation body includes a first detection target shape portion corresponding to the first hole, and another detection target shape portion. The sensor outputs a detection signal in response to detection of each shape portion when the rotation body rotates.

20 Claims, 13 Drawing Sheets

(51) Int. Cl.
*A61B 1/06* (2006.01)
*G02B 23/24* (2006.01)

(58) Field of Classification Search
CPC ............ G02B 21/0028; G02B 21/0052; G02B 21/008; G02B 21/02; G02B 21/025; G02B 21/24; G02B 21/248; G02B 21/36; G02B 21/361
USPC .................................................. 359/368–390
See application file for complete search history.

(56) References Cited

U.S. PATENT DOCUMENTS

| | | | |
|---|---|---|---|
| 6,504,964 B1 * | 1/2003 | Hasegawa | G02B 21/248 385/16 |
| 7,224,522 B2 * | 5/2007 | Kawanabe | G02B 21/16 359/381 |
| 8,368,268 B2 * | 2/2013 | Hasegawa | G02B 21/248 359/381 |
| 2007/0088193 A1 | 4/2007 | Omori et al. | |
| 2007/0263406 A1 | 11/2007 | Negishi | |
| 2013/0109921 A1 | 5/2013 | Masaki et al. | |

FOREIGN PATENT DOCUMENTS

| | | |
|---|---|---|
| JP | S63-189820 A | 8/1988 |
| JP | H03-021219 A | 1/1991 |
| JP | 2001-343595 A | 12/2001 |
| JP | 2006-075240 A | 3/2006 |
| JP | 2007-301211 A | 11/2007 |
| WO | 2005/112737 A1 | 12/2005 |
| WO | 2012/008489 A1 | 1/2012 |

* cited by examiner

ENDOSCOPE ILLUMINATION LIGHT SWITCHING DEVICE AND ENDOSCOPE ILLUMINATION LIGHT SWITCHING METHOD

CROSS REFERENCE TO RELATED APPLICATION

This application is a continuation application of PCT/JP2018/039395 filed on Oct. 23, 2018, the entire contents of which are incorporated herein by this reference.

BACKGROUND OF THE INVENTION

1. Field of the Invention

The present invention relates to an endoscope illumination light switching device, more specifically, an endoscope illumination light switching device configured to switch hole parts and optical filters through which illumination light is transmitted by rotating a turret provided with the hole parts and the optical filters, and an endoscope illumination light switching method.

2. Description of the Related Art

An endoscope system including an endoscope including an image pickup device configured to pick up an image of an object inside a subject, an image processing device as what is called a video processor configured to generate an observation image of the object picked up by the endoscope, and a light source device configured to generate and emit illumination light with which the subject is to be irradiated by the endoscope has been widely used in medical and industrial fields and the like.

A known light source device in such an endoscope system has, for example, a function to generate and emit light of a plurality of different wavelength bands as illumination light, or a function to generate and emit excitation light for autofluorescence observation in addition to light of a visible light wavelength band as normal light.

To switch and emit a plurality of kinds of light, another known light source device includes a filter switching mechanism including a turret in which a plurality of optical filters are disposed, the filter switching mechanism being configured to select a desired optical filter by rotating the turret and switch and emit the plurality of kinds of light. For example, Japanese Patent Application Laid-Open Publication No. 63-189820 and Japanese Patent Application Laid-Open Publication No. 3-021219 disclose light source devices including a filter switching mechanism as described above.

The above-described light source device including a mechanism for switching optical filters disposed in a turret includes a predetermined detection mechanism to position, onto an emission optical path, a filter in accordance with usage among the plurality of optical filters in the turret.

For example, in each filter switching mechanism disclosed in Japanese Patent Application Laid-Open Publication No. 63-189820 and Japanese Patent Application Laid-Open Publication No. 3-021219, a plurality of detection target portions corresponding to a plurality of optical filters are provided on a turret, and a plurality of detection units, such as photo-interrupters or photo-reflectors, corresponding to the plurality of respective detection target portions are provided.

The filter switching mechanism performs control to recognize position information of the optical filters based on detection signals outputted from the plurality of detection units (photo-interrupters or photo-reflectors) and stop the turret at a desired position to position an optical filter in accordance with usage on an emission optical path based on the recognized position information of the optical filters.

In such a filter switching mechanism, detection target portions (slits) corresponding to the plurality of optical filters are provided on the turret, and each slit is detected by a light sensor.

In the above-described filter switching mechanism disclosed in Japanese Patent Application Laid-Open Publication No. 63-189820 or Japanese Patent Application Laid-Open Publication No. 3-021219, the plurality of detection target portions corresponding to the plurality of optical filters on the turret and the plurality of detection units corresponding to the plurality of respective detection target portions are provided as described above, position information of the optical filters is recognized based on a combination pattern of detection signals outputted from the plurality of detection units, and the turret is controlled.

SUMMARY OF THE INVENTION

An endoscope illumination light switching device according to an aspect of the present invention includes: a rotation body held to be rotatable about a predetermined rotational axis, the rotation body having a plurality of holes formed side by side in a circumferential direction on a predetermined radius centered at the rotational axis, the rotation body being configured to rotate to switch a hole inserted on an irradiation optical path among the plurality of holes; a drive device configured to rotationally drive the rotation body; a first hole disposed at a predetermined position among the plurality of holes formed in the rotation body, a second hole disposed at a position different from the first hole among the plurality of holes formed in the rotation body; a first detection target shape portion formed in the rotation body at a position corresponding to the first hole; another detection target shape portion formed in the rotation body at a position different from the first detection target shape portion; a sensor disposed outside the rotation body and configured to output detection signals in response to detection of the first detection target shape portion and the other detection target shape portion when the rotation body rotates; and a processor configured to control a stop position of the rotation body based on the detection signals.

An endoscope illumination light switching method according to another aspect of the present invention includes: switching a hole inserted on an irradiation optical path among a plurality of holes by rotating a rotation body held to be rotatable about a predetermined rotational axis and having the plurality of holes formed side by side in a circumferential direction on a predetermined radius centered at the rotational axis; rotationally driving the rotation body by a drive device, wherein a first hole is disposed at a predetermined position among the plurality of holes formed in the rotation body, a second hole is disposed at a position different from the first hole among the plurality of holes formed in the rotation body, a first detection target shape portion is formed in the rotation body at a position corresponding to the first hole, and another detection target shape portion is formed in the rotation body at a position different from the first detection target shape portion; outputting, by a sensor disposed outside the rotation body, detection signals in response to detection of the first detection target shape portion and the other detection target shape portion when the rotation body rotates; and controlling, by a processor, a stop position of the rotation body based on the detection signals, wherein the other detection target shape portion is a detection target shape portion for reference position detection for detecting a predetermined reference position of the rotation body, a reference detection signal in response to detection of the detection target shape portion for reference position detection can be outputted from the sensor, and when a first detection signal in response to detection of the first detection target shape portion is acquired after the reference detection signal is acquired from the sensor, the rotation body is controlled to stop at a predetermined stop position of the first detection target shape portion by the processor.

Another endoscope illumination light switching method according to another aspect of the present invention includes: switching a hole inserted on an irradiation optical path among a plurality of holes by rotating a rotation body held to be rotatable about a predetermined rotational axis and having the plurality of holes formed side by side in a circumferential direction on a predetermined radius centered at the rotational axis; rotationally driving the rotation body by a drive device, wherein a first hole is disposed at a predetermined position among the plurality of holes formed in the rotation body, a second hole is disposed at a position different from the first hole among the plurality of holes formed in the rotation body, a first detection target shape portion is formed in the rotation body at a position corresponding to the first hole, and another detection target shape portion is formed in the rotation body at a position different from the first detection target shape portion; outputting, by a sensor disposed outside the rotation body, detection signals in response to detection of the first detection target shape portion and the other detection target shape portion when the rotation body rotates; and controlling, by a processor, a stop position of the rotation body based on the detection signals, wherein the other detection target shape portion is a second detection target shape portion formed at a position corresponding to the second hole, and the sensor can output a second detection signal in response to detection of the second detection target shape portion when the rotation body rotates.

BRIEF DESCRIPTION OF THE DRAWINGS

FIG. 9 is a flowchart illustrating an initial setting operation of a turret in the filter switching device of the first embodiment at power-on;

FIG. 11 is a flowchart illustrating an initial setting operation of a turret in a filter switching device of a second embodiment of the present invention at power-on;

FIG. 12 is a flowchart illustrating an error check subroutine at the filter switching device of the second embodiment at power-on;

DETAILED DESCRIPTION OF THE PREFERRED EMBODIMENTS

Embodiments of the present invention will be described below with reference to the accompanying drawings.

First Embodiment

Figure 1:
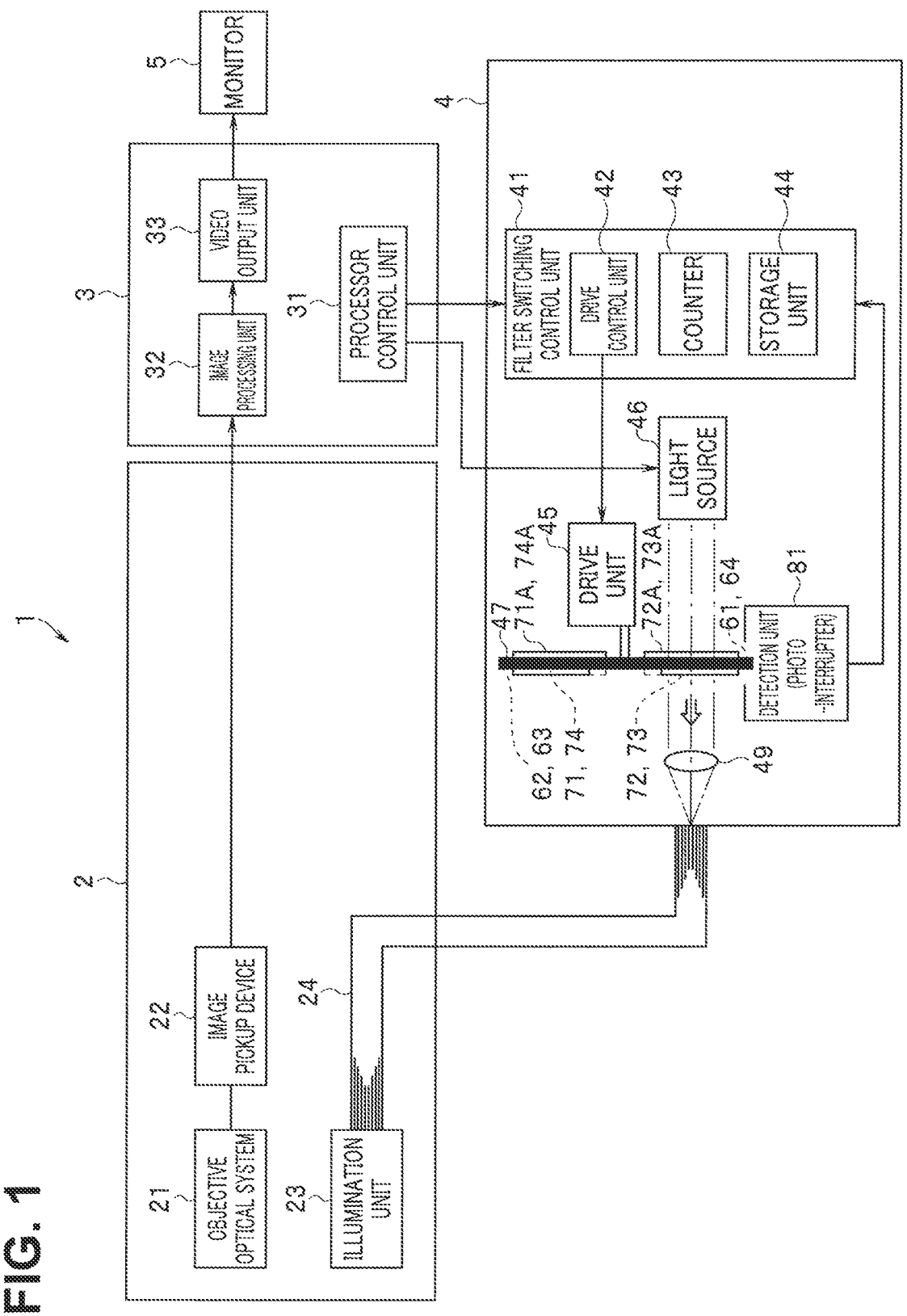
FIG. 1 is a diagram illustrating the configuration of an endoscope system including a filter switching device of a first embodiment of the present invention.
Figure 2:
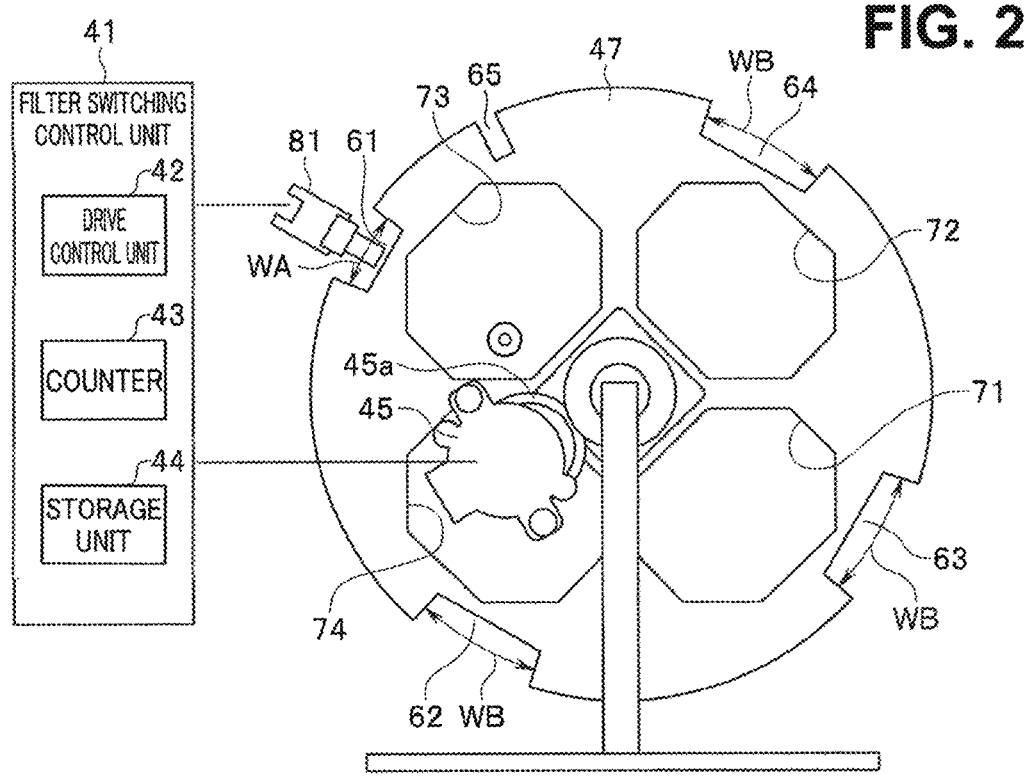
FIG. 2 is a one-side view illustrating one side surface of the filter switching device of the first embodiment together with the configuration of a control unit.
Figure 3:
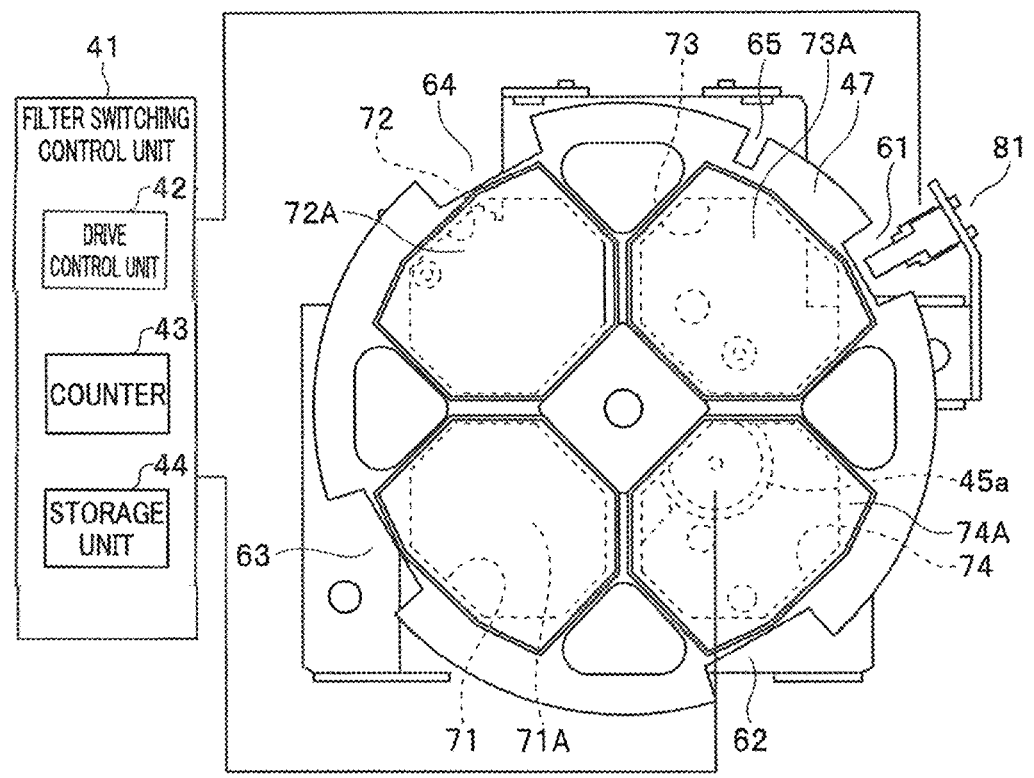
FIG. 3 is a the-other-side view illustrating the other side surface of the filter switching device of the first embodiment together with the configuration of the control unit.

FIG. 1 is a diagram illustrating the configuration of an endoscope system including a filter switching device (endoscope illumination light switching device) of a first embodiment of the present invention. FIG. 2 is a one-side view illustrating one side surface of the filter switching device of the first embodiment together with the configuration of a control unit. FIG. 3 is a the-other-side view illustrating the other side surface of the filter switching device of the first embodiment together with the configuration of the control unit.

As illustrated in FIG. 1, an endoscope system 1 including the filter switching device of the first embodiment includes an endoscope 2 configured to observe a subject and output an image pickup signal, a video processor 3 connected with the endoscope 2 and configured to receive the image pickup signal and provide predetermined image processing to the image pickup signal, a light source device 4 configured to supply illumination light for illuminating the subject, and a monitor device 5 configured to display an observation image in accordance with the image pickup signal.

The endoscope 2 includes an objective optical system 21 disposed at a distal end portion of an insertion portion and including a lens through which an object image is inputted, an image pickup device 22 disposed at an image-forming plane in the objective optical system 21, and an illumination unit 23 capable of irradiating an object with predetermined illumination light.

The image pickup device 22 is configured of, for example, a CMOS image sensor. The image pickup device forms an optical image from the object onto an image pickup surface, photoelectrically converts light incident on each pixel at a photoelectric conversion unit, and outputs a predetermined image pickup signal.

The illumination unit 23 is disposed at a distal end portion of a light guide 24 extending from the light source device 4 to inside of the endoscope 2, and emits illumination light generated at the light source device 4.

In the present embodiment, the video processor 3 includes a processor control unit 31 configured to control various circuits in the video processor 3 as well as the endoscope 2 and the light source device 4 connected with the video processor 3, an image processing unit 32 configured to receive an image signal from the endoscope 2 and provide predetermined image processing to the image signal, and a video output unit 33 configured to receive the image signal processed at the image processing unit 32 and generate a video signal for display on the monitor device 5.

In the present embodiment, the light source device 4 includes a light source 46 configured to generate predetermined illumination light, and in addition, mainly includes a turret 47 configured as the filter switching device, a drive unit 45 (drive device), a filter switching control unit 41, and a detection unit (photo-interrupter) 81 (sensor).

<Light Source in the Present Embodiment>

The following describes the light source 46 disposed in the light source device 4 in which the filter switching device of the present embodiment is provided.

Figure 4:
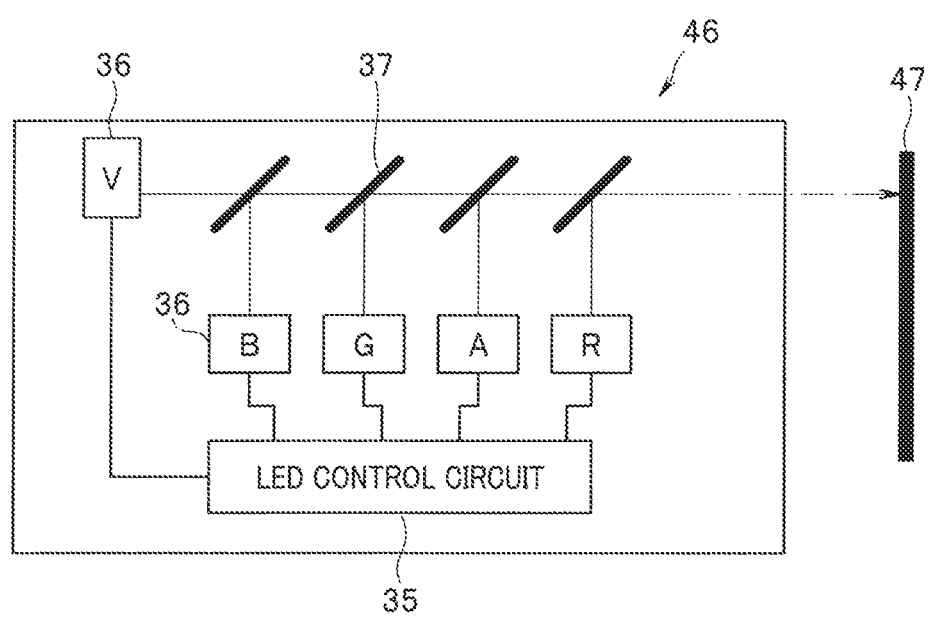
FIG. 4 is a block diagram illustrating an internal configuration of a light source for the filter switching device of the first embodiment.
Figure 5:
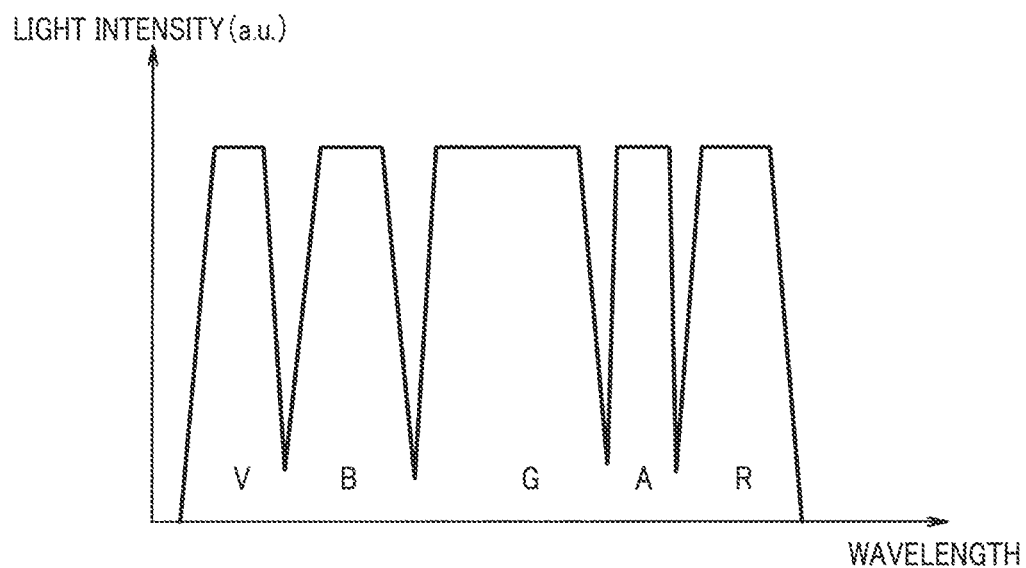
FIG. 5 is a diagram illustrating wavelength characteristics of respective LEDs in the light source for the filter switching device of the first embodiment.

FIG. 4 is a block diagram illustrating an internal configuration of the light source for the filter switching device of the first embodiment, and FIG. 5 is a diagram illustrating wavelength characteristics of respective LEDs in the light source for the filter switching device of the first embodiment.

As illustrated in FIG. 4, the light source 46 in the present embodiment includes five LEDs 36 having colors different from one another. Specifically, the LEDs 36 are configured of five LEDs of V [violet], B [blue], G [green], A [umber], and R [red]. FIG. 5 is a diagram illustrating wavelength characteristics of the respective five LEDs 36.

Light emission from each of the LEDs 36 (V [violet], B [blue], G [green], A [umber], and R [red]) is controlled by an LED control circuit 35. The LED control circuit 35 is connected with the processor control unit 31 of the video processor 3 and controlled by the processor control unit 31 (refer to FIG. 1).

For example, when observation modes are switched by an observation mode switching operation means not illustrated, the LED control circuit 35 is controlled by the processor control unit 31 and controls light emission from the LEDs 36 (V [violet], B [blue], G [green], A [umber], and R [red]) in accordance with each observation mode.

In the light source 46, light emitted from each of the five LEDs 36 (V [violet], B [blue], G [green], A [umber], and R [red]) is outputted toward the turret 47 through a dichroic mirror 37.

The light source 46 in the present embodiment can emit illumination light in accordance with an observation mode. Specifically, the light source 46 can emit illumination light suitable for a WLI observation mode (white illumination mode) or three kinds of special light observation modes (an NBI observation mode, an AFI observation mode, and an RBI observation mode).

Specifically, when the WLI observation mode is selected, the LED control circuit 35 controls all five color LEDs 36 (V [violet], B [blue], G [green], A [umber], and R [red]) described above to emit light (refer to FIG. 5).

The NBI observation mode is an observation mode for observation of a blood vessel at high contrast. When the NBI observation mode is selected, the LED control circuit 35 controls the V [violet] and G [green] LEDs 36 to emit light among the five color LEDs 36 (V [violet], B [blue], G [green], A [umber], and R [red]).

The AFI observation mode is an observation mode for observation of autofluorescence. When the AFI observation mode is selected, the LED control circuit 35 controls the V [violet] and G [green] LEDs 36 to emit light among the five color LEDs 36 (V [violet], B [blue], G [green], A [umber], and R [red]). Note that, in the AFI observation mode, the LED control circuit 35 controls the LEDs 36 so that a light quantity ratio of V [violet] and G [green] is different from the light quantity ratio in the NBI observation mode. Specifically, in the AFI observation mode, the control is performed so that the light quantity of G is lower than the light quantity of V.

The RBI observation mode is an observation mode for improving visibility of a bleeding point or the like. When the RBI observation mode is selected, the LED control circuit 35 controls the G [green], A [umber], and R [red] LEDs 36 to emit light among the five color LEDs 36 (V [violet], B [blue], G [green], A [umber], and R [red]).

Each illumination light generated by the light source 46 is emitted toward the turret 47. The illumination light is emitted from the illumination unit 23 of the endoscope 2 through an optical filter placed on an irradiation optical path in the turret 47 and through a light condensation lens 49 and the light guide 24.

Note that illumination light having a wavelength (color) selected in accordance with each observation mode (the WLI observation mode, the NBI observation mode, the AFI observation mode, or the RBI observation mode) is emitted from the light source 46 as described above, but in the light source device 4 according to the present embodiment, a plurality of kinds (in the present embodiment, four kinds) of optical filters that partially dim or shield the above-described illumination light emitted from the light source 46 in accordance with an observation mode are disposed in the turret to further improve performance of observation lights (WLI light, NBI light, AFI light, and RBI light) corresponding to the respective above-described observation modes. The optical filters and the turret will be described later in detail.

<Filter Switching Device>

Subsequently, the filter switching device of the first embodiment will be described below with reference to FIGS. 2 and 3 in addition to FIG. 1. FIG. 2 is a one-side view illustrating one side surface of the filter switching device of the first embodiment together with the configuration of the control unit, and FIG. 3 is a the-other-side view illustrating the other side surface of the filter switching device of the first embodiment together with the configuration of the control unit.

The filter switching device in the present embodiment includes the turret 47, the drive unit (stepping motor) 45, the filter switching control unit 41, and the detection unit (photo-interrupter) 81 as described above.

<Turret and Hole Parts (Holes)>

As illustrated in FIGS. 2 and 3, a plurality of hole parts (a first hole part 71, a second hole part 72, a third hole part 73, and a fourth hole part 74) held to be rotatable about a predetermined rotational axis and provided side by side in the circumferential direction on the predetermined radius centered at the rotational axis are formed in the turret 47.

The turret 47 rotates about the rotational axis to switch a hole part inserted on the irradiation optical path from the light source 46 among the plurality of holes (the first hole part 71, the second hole part 72, the third hole part 73, and the fourth hole part 74).

Note that, in the present embodiment, the plurality of hole parts (the first hole part 71, the second hole part 72, the third hole part 73, and the fourth hole part 74) are provided side by side on the predetermined radius in the order of the first hole part 71, the second hole part 72, the third hole part 73, and the fourth hole part 74 in the circumferential direction with reference to the first hole part 71 disposed at a predetermined position in the turret 47 as illustrated in FIG. 2.

<Wli Filter>

In the present embodiment, a first optical filter 71A (WLI filter) configured of, for example, a transparent glass filter is disposed at the first hole part 71 disposed at the predetermined position among the four hole parts in the turret 47 to cover the hole part (refer to FIG. 3).

When the first hole part 71 is positioned on the irradiation optical path, the first optical filter 71A (WLI filter) transmits white light from the light source 46, thereby enabling what is called white light imaging (WLI) observation.

Note that, in the present embodiment, for example, the first optical filter 71A (WLI filter) configured of a transparent glass filter is disposed at the first hole part 71 as described above, but the present invention is not limited to this configuration. For example, no predetermined optical filter may be provided so that white light from the light source 46 is directly transmitted when the first hole part 71 is positioned on the irradiation optical path.

<Special Observation Filters>

In the present embodiment, a second optical filter 72A, a third optical filter 73A, and a fourth optical filter 74A are provided to the second hole part 72, the third hole part 73, and the fourth hole part 74 among the four hole parts in the turret 47, respectively, disposed at predetermined positions as illustrated in FIG. 3 to cover the hole parts.

The second optical filter 72A, the third optical filter 73A, and the fourth optical filter 74A are what is called special observation filters, and are a narrow band imaging filter (NBI filter) 72A, an autofluorescence imaging filter (AFI filter) 73A, and a red band imaging filter (RBI filter) 74A, respectively, in the present embodiment.

<Nbi Filter>

Figure 6:
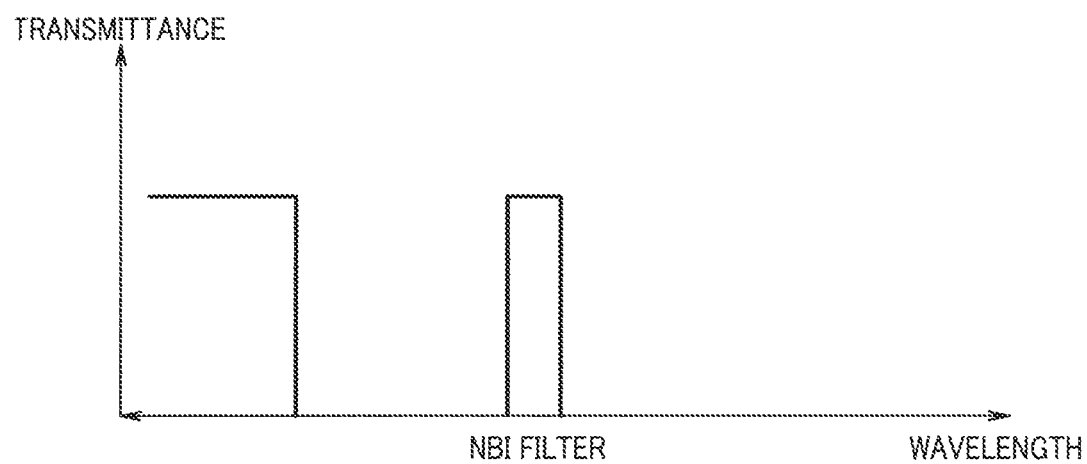
FIG. 6 is a diagram illustrating a filter wavelength characteristic of an NBI filter in the filter switching device of the first embodiment.

FIG. 6 is a diagram illustrating a filter wavelength characteristic of an NBI filter in the filter switching device of the first embodiment. As described above, the second optical filter 72A is configured of an NBI filter in the present embodiment.

As illustrated in FIG. 6, the NBI filter 72A (second optical filter 72A) is an optical filter that partially dims or shields the above-described illumination light emitted from the light source 46 in accordance with the NBI observation mode to further improve performance of NBI light corresponding to the NBI observation mode. Specifically, the NBI filter 72A transmits a V [violet] color beam and narrowed-band light of a G [green] color beam.

Note that the NBI observation mode is an observation mode for observation of a blood vessel at high contrast. In the present embodiment as described above, when the NBI observation mode is selected, the light source 46 emits illumination light corresponding to selection of V [violet] and G [green] among the five color LEDs 36 (V [violet], B [blue], G [green], A [umber], and R [red]).

<Afi Filter>

Figure 7:
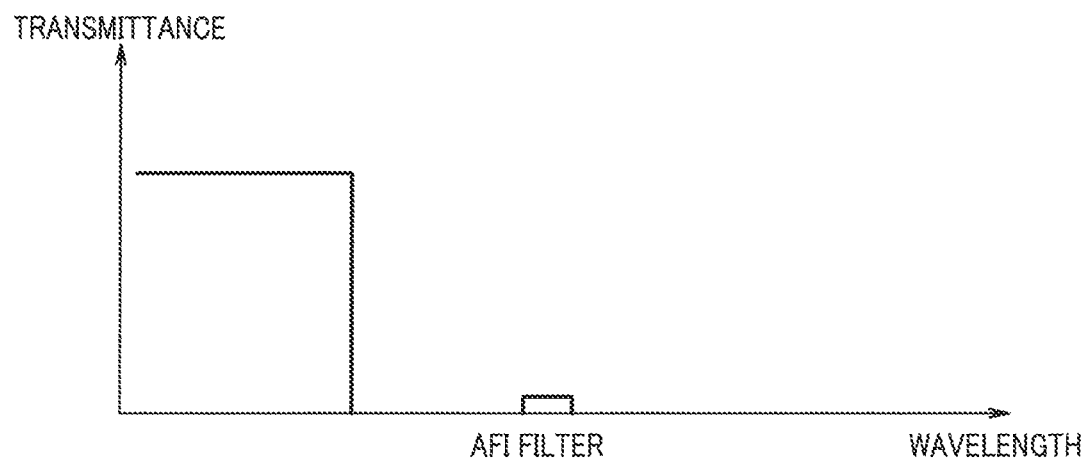
FIG. 7 is a diagram illustrating a filter wavelength characteristic of an AFI filter in the filter switching device of the first embodiment.

FIG. 7 is a diagram illustrating a filter wavelength characteristic of an AFI filter in the filter switching device of the first embodiment. As described above, the third optical filter 73A is configured as an AFI filter in the present embodiment.

As illustrated in FIG. 7, the AFI filter 73A (third optical filter 73A) is an optical filter that partially dims or shields the above-described illumination light emitted from the light source 46 in accordance with the AFI observation mode to further improve performance of AFI light corresponding to the AFI observation mode. Specifically, the AFI filter 73A transmits a V [violet] color beam and dimmed and narrowed-band light of a G [green] color beam.

The AFI observation mode is an observation mode for observation of autofluorescence. In the present embodiment as described above, when the AFI observation mode is selected, the light source 46 emits illumination light corresponding to selection of V [violet] and G [green] among the five color LEDs 36 (V [violet], B [blue], G [green], A [umber], and R [red]).

<Rbi Filter>

Figure 8:
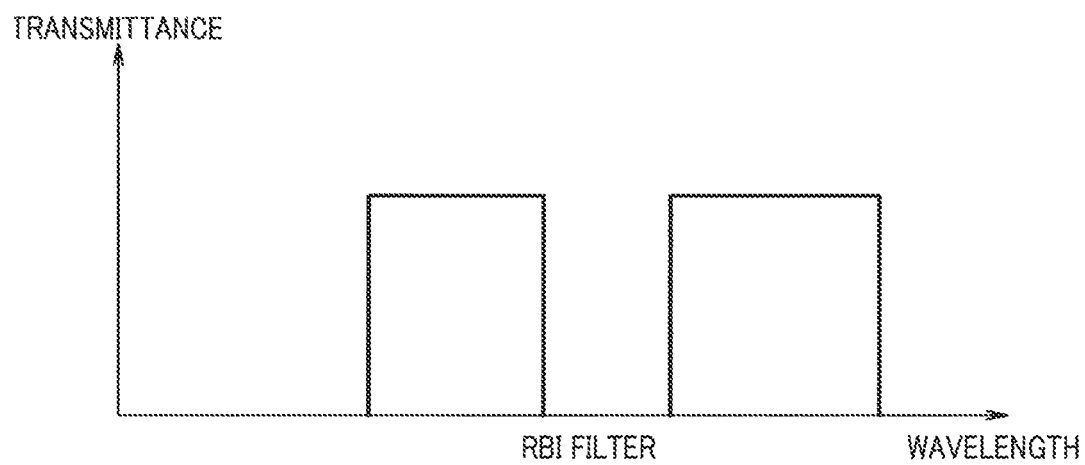
FIG. 8 is a diagram illustrating a filter wavelength characteristic of an RBI filter in the filter switching device of the first embodiment.

FIG. 8 is a diagram illustrating a filter wavelength characteristic of an RBI filter in the filter switching device of the first embodiment. As described above, the fourth optical filter 74A is configured as an RBI filter in the present embodiment.

As illustrated in FIG. 8, the RBI filter 74A (fourth optical filter 74A) is an optical filter that partially dims or shields the above-described illumination light emitted from the light source 46 in accordance with the RBI observation mode to further improve performance of RBI light corresponding to the RBI observation mode. Specifically, the RBI filter 74A transmits a B [blue] color beam, an A [umber] color beam, and an R [red] color beam.

The RBI observation mode is an observation mode for improving visibility of a bleeding point or the like. In the present embodiment as described above, when the RBI observation mode is selected, the light source 46 emits illumination light corresponding to selection of G [green], A [umber], and R [red] among the five color LEDs 36 (V [violet], B [blue], G [green], A [umber], and R [red]).

Note that, in the present embodiment, the second optical filter 72A, the third optical filter 73A, and the fourth optical filter 74A are special observation filters, but not limited to this configuration and may be various kinds of optical filters.

<Detection Target Slits (Detection Target Shape Portions)>

As illustrated in FIGS. 2 and 3, in the present embodiment, a plurality of (in the present embodiment, four) cutout portions are formed at a periphery portion of the turret 47 and serve as a first slit 61, a second slit 62, a third slit 63, and a fourth slit 64, respectively.

In the present embodiment, an additional cutout portion is formed near the first slit 61 at the periphery portion of the turret 47 and serves a reference position detection slit 65 (detection target shape portion for reference position detection) for defining a reference position.

Note that the cutout portions (the first slit 61, the second slit 62, the third slit 63, the fourth slit 64, and the reference position detection slit 65) each have the shape of a cut along two straight lines extending in the radial direction from the rotation center of the turret 47 and an arc on the predetermined radius at an outer peripheral part of the turret 47.

The first slit 61, the second slit 62, the third slit 63, and the fourth slit 64 are disposed at positions corresponding to the first hole part 71, the second hole part 72, the third hole part 73, and the fourth hole part 74, respectively, in the turret 47.

Further, the first slit 61, the second slit 62, the third slit 63, and the fourth slit 64 each have the following correspondence.

The first slit 61: the first optical filter 71A (WLI filter 71A)

The second slit 62: the second optical filter 72A (NBI filter 72A)

The third slit 63: the third optical filter 73A (AFI filter 73A)

The fourth slit 64: the fourth optical filter 74A (RBI filter 74A)

Specifically in the first embodiment, as for the disposition positions of the hole parts, the pairs of the first slit 61 and the first hole part 71, the second slit 62 and the second hole part 72, the third slit 63 and the third hole part 73, and the fourth slit 64 and the fourth hole part 74 are each disposed at positions symmetric with respect to the rotational axis.

The reference position detection slit 65 is formed near the first slit 61 between the first slit 61 and the fourth slit 64 at the periphery portion of the turret 47.

The first slit 61, the second slit 62, the third slit 63, the fourth slit 64, and the reference position detection slit 65 are formed to have predetermined width dimensions, respectively, in the circumferential direction on the predetermined radius centered at the rotational axis of the turret 47.

Specifically in the first embodiment, when the angle of the turret 47 in the circumferential direction is represented by [deg] and the number of steps of the stepping motor to be described later is represented by [step], the reference position detection slit 65, the first slit 61, the second slit 62, the third slit 63, and the fourth slit 64 each have the following width dimensions.

The reference position detection slit 65: WIni (5 [deg](10 [step]))

The first slit 61: WA (15 [deg](30 [step]))

The second slit 62: WB (25 [deg](50 [step]))

The third slit 63: WB (25 [deg](50 [step]))

The fourth slit 64: WB (25 [deg](50 [step]))

<Drive Unit (Stepping Motor) 45>

In the present embodiment, the turret 47 is driven by the stepping motor as the drive unit (refer to FIG. 1). Specifically, the drive unit (stepping motor) 45 (hereinafter also referred to as the stepping motor 45) is capable of rotational driving in both directions and rotationally drives the turret 47 as a rotation body through a predetermined gear unit 45a as illustrated in FIG. 2. Note that drive of the stepping motor 45 is controlled by a drive control unit 42 of the filter switching control unit 41.

<Detection Unit (Photo-Interrupter) 81 (Sensor)>

The detection unit (photo-interrupter) 81 (hereinafter also referred to as the photo-interrupter 81) is a detection unit (light sensor) configured to detect the reference position detection slit 65, the first slit 61, the second slit 62, the third slit 63, or the fourth slit 64, has functions of a well-known photo-interrupter, in other words, has a predetermined "detection region", and is disposed outside the turret 47 in the present embodiment.

Note that, in the present embodiment, the detection unit is a photo-interrupter as a light sensor, but may be any other light sensor such as a photo-reflector.

As illustrated in FIG. 3, the photo-interrupter 81 is fixed to a predetermined housing unit and detects any of the reference position detection slit 65, the first slit 61, the second slit 62, the third slit 63, and the fourth slit 64 formed as cutout portions when the slit passes through the predetermined detection region described above as the turret 47 rotates.

When the photo-interrupter 81 detects the reference position detection slit 65 as the turret 47 rotates, the photo-interrupter 81 outputs a "reference position slit detection signal (reference detection signal)" during passing through the detection region.

When the photo-interrupter 81 detects the first slit 61 as the turret 47 rotates, the photo-interrupter 81 outputs a "first slit detection signal" as a first detection signal. Similarly, when the photo-interrupter 81 detects the second slit 62, the third slit 63, or the fourth slit 64 as the turret 47 rotates, the photo-interrupter 81 outputs a "second slit detection signal", a "third slit detection signal", or a "fourth slit detection signal", respectively.

The signals ("reference position slit detection signal", "first slit detection signal", "second slit detection signal", "third slit detection signal", and "fourth slit detection signal") outputted from the photo-interrupter 81 are inputted to the filter switching control unit 41.

<Filter Switching Control Unit 41 (Processor of Light Source Device 4)>

Subsequently, the filter switching control unit 41 configured as the filter switching device in the present embodiment will be specifically described below.

The filter switching control unit 41 is disposed in the light source device 4 as illustrated in FIGS. 1 to 3. The filter switching control unit 41 includes the drive control unit 42 configured to control rotation of the turret 47 by driving the stepping motor 45, a counter 43 configured to count the number of steps of the stepping motor 45, and a storage unit 44 (memory) storing various kinds of information of each slit. The filter switching control unit 41 as a processor is configured of, for example, a field programmable gate array (FPGA). However, the present invention is not limited to this configuration, and the processor may include a CPU, a ROM, and a RAM and achieve all or some functions of each functional component as the CPU reads a computer program (software) stored in the ROM, loads the computer program onto the RAM, and executes the computer program. All or some functional components of the processor may be configured of electronic circuits.

<Drive Control Unit of Stepping Motor>

The drive control unit 42 is configured as a circuit formed in what is called a field-programmable gate array (FPGA) in the present embodiment, and controls step drive of the stepping motor 45 under control of the processor control unit 31 of the video processor 3 so that a desired optical filter among the optical filters disposed at the turret 47 is placed at an appropriate position on the optical path of illumination light emitted from the light source 46.

The drive control unit 42 is connected with an output end of the photo-interrupter 81 (detection unit) and has functions of a detection signal input unit configured to receive the detection signals ("reference position slit detection signal", "first slit detection signal", "second slit detection signal", "third slit detection signal", and "fourth slit detection signal") outputted from the photo-interrupter 81 (detection unit).

The drive control unit 42 is also connected with the processor control unit 31 of the video processor 3 and has a function to receive a filter switching instruction signal from the observation mode switching operation means not illustrated through the video processor 3.

In the present embodiment, the counter 43 has a function to count, under control of the drive control unit 42, the number of steps transmitted from the drive control unit 42 toward the stepping motor 45 under a predetermined condition. Details of this function will be described later.

The storage unit 44 (memory) stores various kinds of information of the slits (the reference position detection slit 65, the first slit 61, the second slit 62, the third slit 63, and the fourth slit 64). Specifically, the storage unit 44 first stores information of the slit width of each slit.

More specifically, in the first embodiment, the storage unit 44 stores the numbers of steps corresponding to the width dimensions of the reference position detection slit 65, the first slit 61, the second slit 62, the third slit 63, and the fourth slit 64 in such a way that the reference position detection slit 65: 10 [step](5 [deg]),
the first slit 61: 30 [step](15 [deg]),
the second slit 62: 50 [step](25 [deg]),
the third slit 63: 50 [step](25 [deg]), and
the fourth slit 64: 50 [step](25 [deg]), respectively. In the above, the number of steps of the stepping motor is represented by [step], and the angle of the turret 47 in the circumferential direction is represented by [deg].

In addition, in the present embodiment, the storage unit 44 stores the position of each of the first slit 61, the second slit 62, the third slit 63, and the fourth slit 64 with respect to the reference position defined by the reference position detection slit 65 in association with width information (for example, the number of steps, the angle of the slit, and a time period for which the stepping motor is operated) of the slit.

In addition, in the present embodiment, the storage unit 44 stores relative position information (for example, the number of steps) of a slit (the second slit 62, the third slit 63, or the fourth slit 64) with respect to the first slit 61 (WLI slit) in association with the width dimension of the slit.

Effects of Filter Switching Device of First Embodiment

Subsequently, effects of the filter switching device of the present embodiment will be described below with reference to FIGS. 9 and 10.

<Initial Setting Operation at Power-on of Main Body>

The following first describes initial setting operation of the turret in the filter switching device of the first embodiment at power-on.

Figure 9:
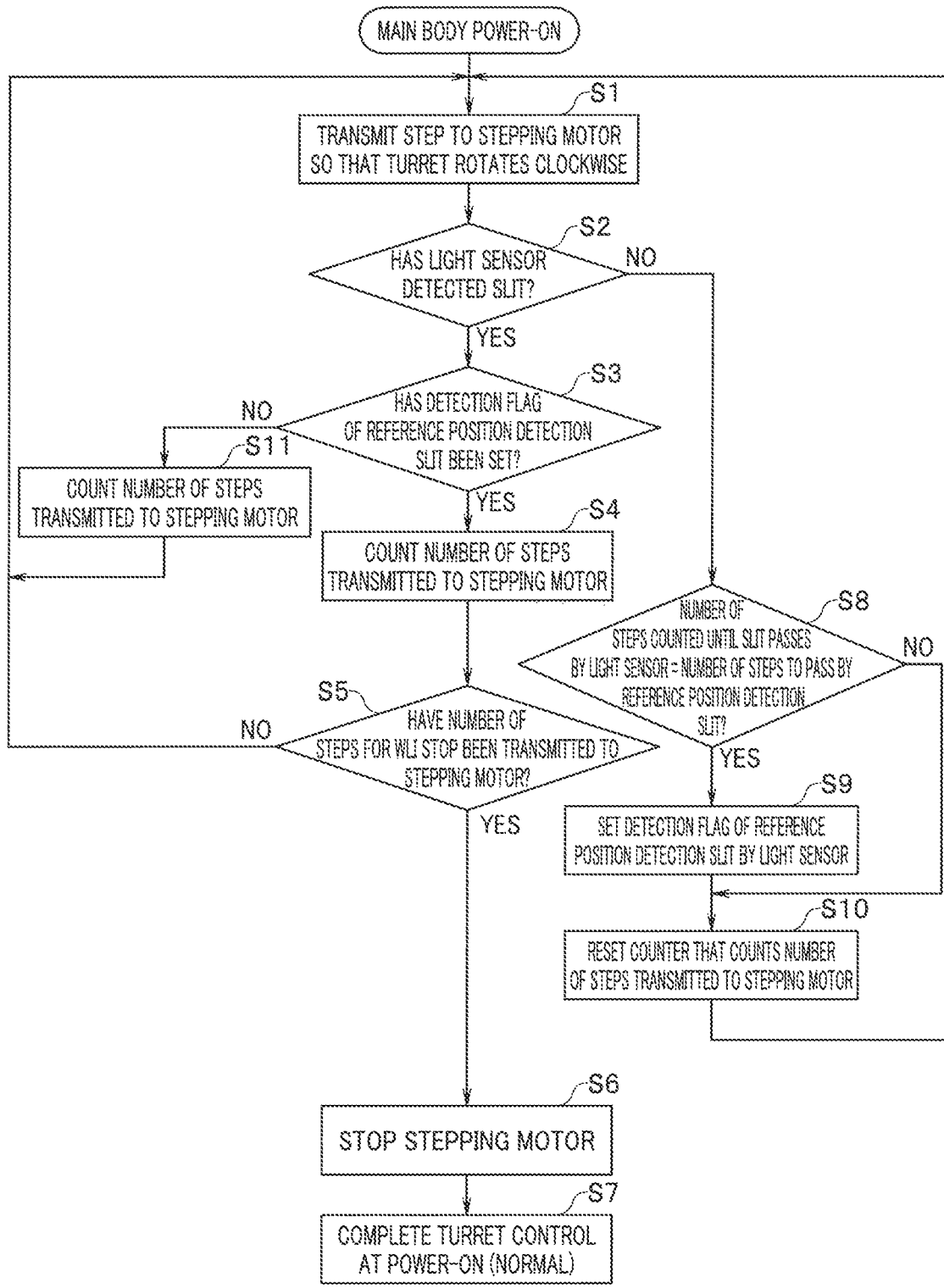

FIG. 9 is a flowchart illustrating the initial setting operation of the turret in the filter switching device of the first embodiment at power-on.

First, after main bodies of the video processor 3 and the light source device 4 is powered on (main body power-on), the drive control unit 42 of the filter switching control unit 41 transmits, as initial operation, a predetermined step to the stepping motor 45 for rotational driving so that the turret 47 rotates clockwise in FIG. 2 (step S1).

While controlling the stepping motor 45 to rotate the turret 47, the drive control unit 42 determines whether any slit detection signal (the reference position slit detection signal, the first slit detection signal, the second slit detection signal, the third slit detection signal, or the fourth slit detection signal) has been acquired from the photo-interrupter 81 (light sensor) (whether or not any slit has been detected) (step S2).

The photo-interrupter 81 has not detected a slit yet right after rotation of the turret 47, and thus the drive control unit 42 proceeds to step S8 and compares the number of steps counted by the counter 43 and the number of steps corresponding to the slit width of the reference position detection slit 65. In this case, the counter 43 is yet to start counting, and thus the drive control unit 42 proceeds to step S10, temporarily resets the counter, and then continues further rotation of the turret 47.

When the photo-interrupter 81 has detected any slit at the above-described step S2, the drive control unit 42 subsequently determines whether a detection flag of the reference position detection slit 65 has been set (step S3). Specifically, the drive control unit 42 determines whether the reference position detection slit 65 has passed by the photo-interrupter 81.

When the flag has not been set at step S3, the drive control unit 42 proceeds to step S1, activates the counter 43 to start counting the number of steps transmitted to the stepping motor 45 (step S11), and continues further rotation of the turret 47.

Thereafter, the drive control unit 42 continues monitoring a detection signal from the photo-interrupter 81 and continues further rotation of the turret 47 until acquisition of the detection signal of the slit from the photo-interrupter 81 ends. Note that the counter 43 continues counting in this case.

When having received a notification that acquisition of the detection signal of the slit from the photo-interrupter 81 has ended during monitoring of the detection signal from the photo-interrupter 81 (step S2), at step S8, the drive control unit 42 compares the number of steps counted by the counter 43 and the number of steps corresponding to the slit width of the reference position detection slit 65 (step S8).

At step S8, when the counted number of steps is equal to the number of steps corresponding to the slit width of the reference position detection slit 65 (in the present embodiment, 10 [step] as described above), the drive control unit 42 determines that the reference position detection slit 65 has passed by the photo-interrupter 81, and sets the detection flag of the reference position detection slit 65 (step S9).

Thereafter, the drive control unit 42 temporarily resets counting by the counter 43 (step S10) and controls the stepping motor 45 to continue rotation of the turret 47 again (step S1).

When having acquired the next slit detection signal from the photo-interrupter 81 (step S2), the drive control unit 42 determines again whether the detection flag of the reference position detection slit 65 has been set (step S3).

Since the detection flag of the reference position detection slit 65 has been set at step S9 described above, the drive control unit 42 proceeds from the present step S3 to step S4.

Note that, in the present embodiment, a slit first detected by the photo-interrupter 81 after having detected the reference position detection slit 65 as the turret 47 rotates clockwise in FIG. 2 is set to be the first slit 61 (WLI slit) due to the relation among the disposition positions of the slits at the turret 47.

The slit first detected by the photo-interrupter 81 after having detected the reference position detection slit 65 is set to be the first slit 61 (WLI slit) corresponding to the first optical filter 71A (WLI filter 71A) because the initial position of the turret 47 is defined to be a state in which the first optical filter 71A (WLI filter 71A) is placed on the optical path of illumination light emitted from the light source 46 in the present embodiment as described later.

That is, the slit first detected after the reference position detection slit 65 has passed by the photo-interrupter 81 and the detection flag of the reference position detection slit 65 has been set is the first slit 61. Thus, a slit currently detected by the photo-interrupter 81 is the first slit 61 as well.

At the timing when the photo-interrupter 81 has detected the first slit 61 (in this case, the photo-interrupter 81 first detects an edge of the first slit 61 and outputs the first slit detection signal), the drive control unit 42 activates the counter 43 again and starts counting (step S4).

Thereafter, the drive control unit 42 transmits, to the stepping motor 45 based on slit width information of the first slit 61 (WLI slit) stored in the storage unit 44, the number of steps for stopping the first slit 61 (WLI slit) at a predetermined stop position (the number of steps until the position corresponding to the detection signal outputted from the photo-interrupter 81 substantially reaches the center of the slit since the photo-interrupter 81 has detected the edge of the first slit 61) (step S5).

Specifically, the first slit 61 (WLI slit) has a step width of 15 [deg] and 30 [step] in the present embodiment, and thus the number of steps for stopping the first slit 61 at the predetermined stop position is 15 [step], which is half of the step width. Accordingly, the drive control unit 42 transmits the number of steps, 15 [step], to the stepping motor 45 at step S5 in the present embodiment.

After having transmitted the number of steps (15 [step]) to the stepping motor 45, the drive control unit 42 stops the stepping motor 45 (step S6). In this case, the first optical filter 71A (WLI filter 71A) corresponding to the first slit 61 (WLI slit) stops at a position on the optical path of illumination light emitted from the light source 46. Accordingly, control of the initial operation of the turret 47 is completed (step S7).

Note that, in the present embodiment, the initial position of the turret 47 is defined to be a state in which the first optical filter 71A (WLI filter 71A) is placed on the optical path of illumination light emitted from the light source 46.

<Operation when Filter Switching is Instructed by User>

The following describes operation in the filter switching device of the first embodiment when filter switching is instructed by a user.

Figure 10:
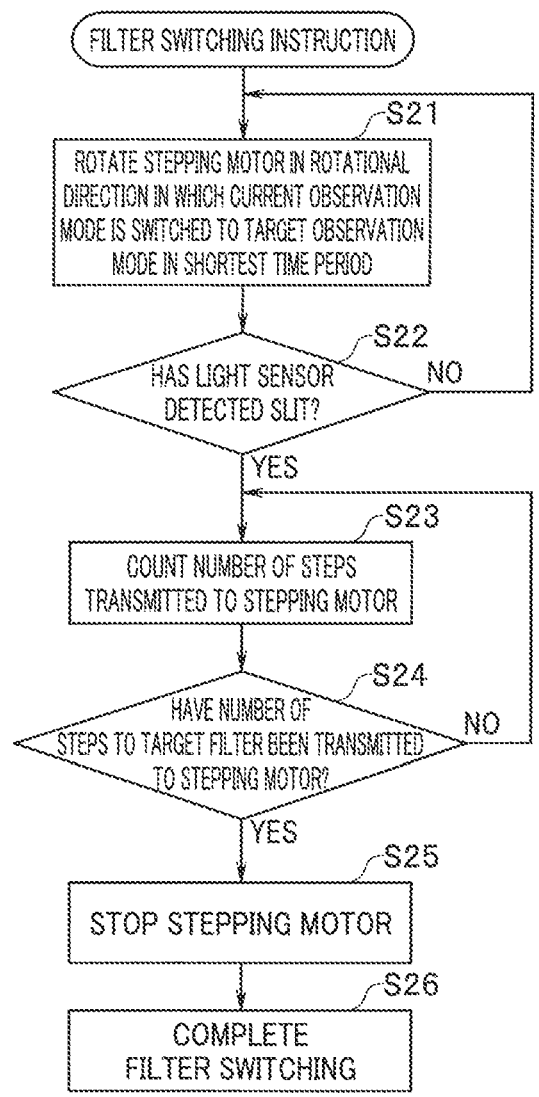
FIG. 10 is a flowchart illustrating a turret control operation in the filter switching device of the first embodiment when filter switching is instructed.

FIG. 10 is a flowchart illustrating turret control operation in the filter switching device of the first embodiment when filter switching is instructed.

When observation modes are switched by the observation mode switching operation means not illustrated, the drive control unit 42 receives an optical filter switching instruction through the processor control unit 31 of the video processor 3 or the like.

In the present embodiment, the storage unit 44 stores various kinds of information of each slit, for example, information of the slit width of the slit as described above and also stores relative position information (for example, the number of steps) of any other slit (the second slit 62, the third slit 63, or the fourth slit 64) relative to the first slit 61 (WLI slit) in association with the width dimension of the slit.

Specifically, the storage unit 44 stores the distance from the stop position of the first slit 61 to the stop position of the second slit 62, the third slit 63, or the fourth slit 64 as the rotation angle ([deg]) of the turret 47 and the number of steps of the stepping motor 45. The storage unit 44 stores the rotation angle ([deg]) of the turret 47 and the number of steps of the stepping motor 45 in association with information of the width dimension of each slit.

In the present embodiment, the storage unit 44 also stores a placement relation corresponding to each observation mode and may store a rotational direction, a rotational amount, and the like.

When having received an instruction to switch the turret 47 to a targeted stop position, the drive control unit 42 controls, based on the relative position information stored in the storage unit 44, the stepping motor 45 to rotate the turret 47 so that the turret 47 reaches the targeted stop position from the current position by a smallest rotational amount.

Specifically, assume that the turret 47 is currently stopping at the above-described initial position. In this case, in the present embodiment, the first optical filter 71A (WLI filter 71A) is positioned on the optical path of illumination light emitted from the light source 46, and the first slit 61 corresponding to the first optical filter 71A is stopping while the position of detection by the photo-interrupter 81 is substantially at the center of the slit width of the first slit 61.

Then, for example, the NBI observation mode is selected as the observation mode while the turret 47 is stopping at the initial position. In this case, the drive control unit 42 receives, from the processor control unit 31, an instruction to switch the observation mode from the WLI observation mode to the NBI observation mode, in other words, an instruction to switch the optical filter placed on the illumination light optical path from the first optical filter 71A (WLI filter 71A) to the second optical filter 72A (NBI filter 72A).

Having received the instruction, the drive control unit 42 controls rotation of the stepping motor 45 so that the first optical filter 71A corresponding to the current observation mode (in this example, the WLI observation mode) is switched to the second optical filter 72A corresponding to a target observation mode (in this example, the NBI observation mode) by a smallest rotational amount (in a shortest time period) in the turret 47 (step S21).

In this case, the drive control unit 42 acquires relative position information on the stop position of the first slit 61 (corresponding to the first optical filter 71A) and the stop position of the second slit 62 (second optical filter 72A), which is stored in the storage unit 44, derives, based on the information, the rotational direction of the turret 47 and the number of steps of the stepping motor 45 with which the second slit 62 is reached by a smallest rotational amount, and controls rotation of the turret 47 in accordance with the derived rotational direction and the derived number of steps.

The drive control unit 42 rotates the turret 47 in the rotational direction by the number of steps necessary for reaching the second slit 62 corresponding to the target filter (the second optical filter 72A) by the smallest rotational amount. Thereafter, when the photo-interrupter 81 has detected the second slit 62 (step S22), the drive control unit 42 activates the counter 43 again to start counting the number of steps to be transmitted to the stepping motor 45 (step S23).

Thereafter, the drive control unit 42 transmits, to the stepping motor 45, the number of steps in accordance with the stop position of the second slit 62 corresponding to the target filter (second optical filter 72A) (the number of steps until the position corresponding to the detection signal outputted from the photo-interrupter 81 substantially reaches the center of the slit since the photo-interrupter 81 has detected an edge of the second slit 62).

Specifically, the second slit 62 (NBI slit) has a step width of 25 [deg] and 50 [step] in the present embodiment, and thus the number of steps for stopping the second slit 62 at a predetermined stop position is 25 [step], which is half of the step width. Accordingly, in this case, the drive control unit 42 transmits the number of steps, 25 [step], to the stepping motor 45 in the present embodiment.

Thereafter, when the number of counts by the counter 43 reaches the number of steps (25 [step]) (step S24), the drive control unit 42 stops the stepping motor 45 (step S25).

In this case, the second optical filter 72A (NBI filter 72A) corresponding to the second slit 62 (NBI slit) stops at a position on the optical path of illumination light emitted from the light source 46. Accordingly, control of the optical filter switching operation is completed (step S26).

As described above, with the filter switching device of the first embodiment, the position of an optical filter on the turret can be recognized only by a single detection unit such as a photo-interrupter without a plurality of detection units, and the optical filter can be accurately placed at a desired position in a short time period.

Second Embodiment

Subsequently, a second embodiment of the present invention will be described below.

A filter switching device of the second embodiment has a main configuration same as the configuration of the first embodiment but is characterized in that an error check subroutine is executed in the initial setting operation of the turret 47. Other configurations and effects are same as the configurations and effects of the first embodiment, and thus only difference from the first embodiment will be described below, and any common part will not be described.

Figure 11:
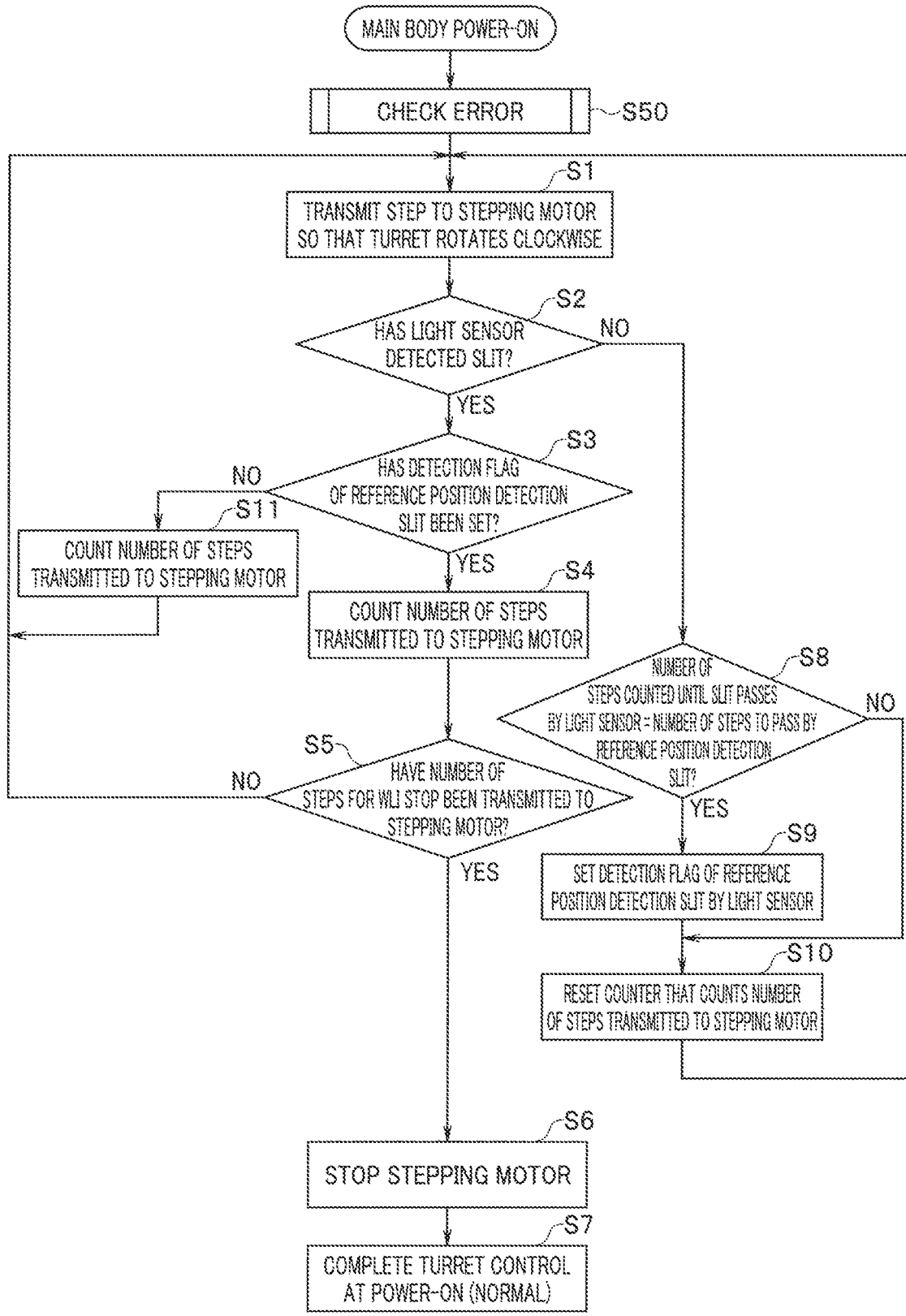
Figure 12:
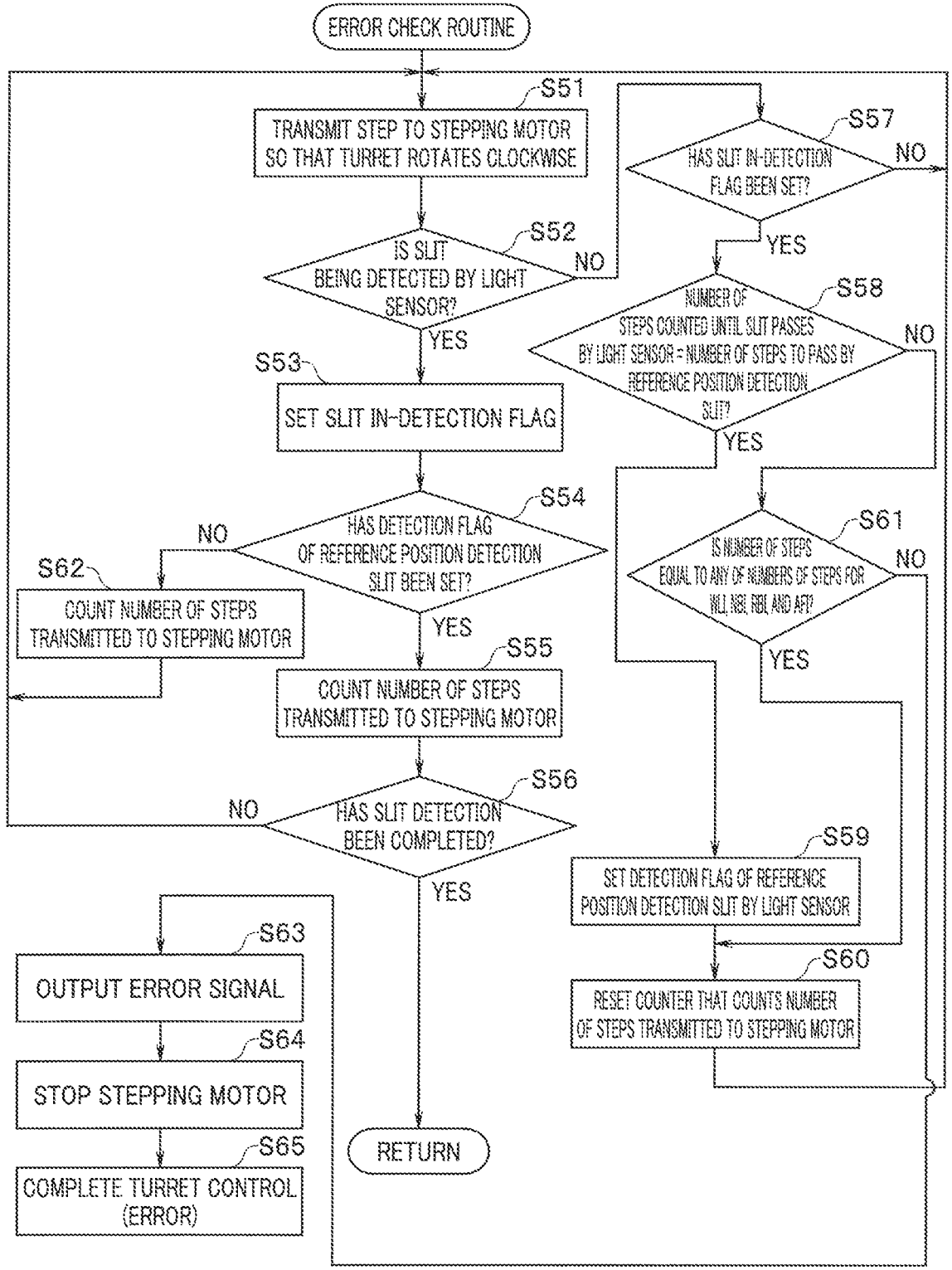
Figure 13:
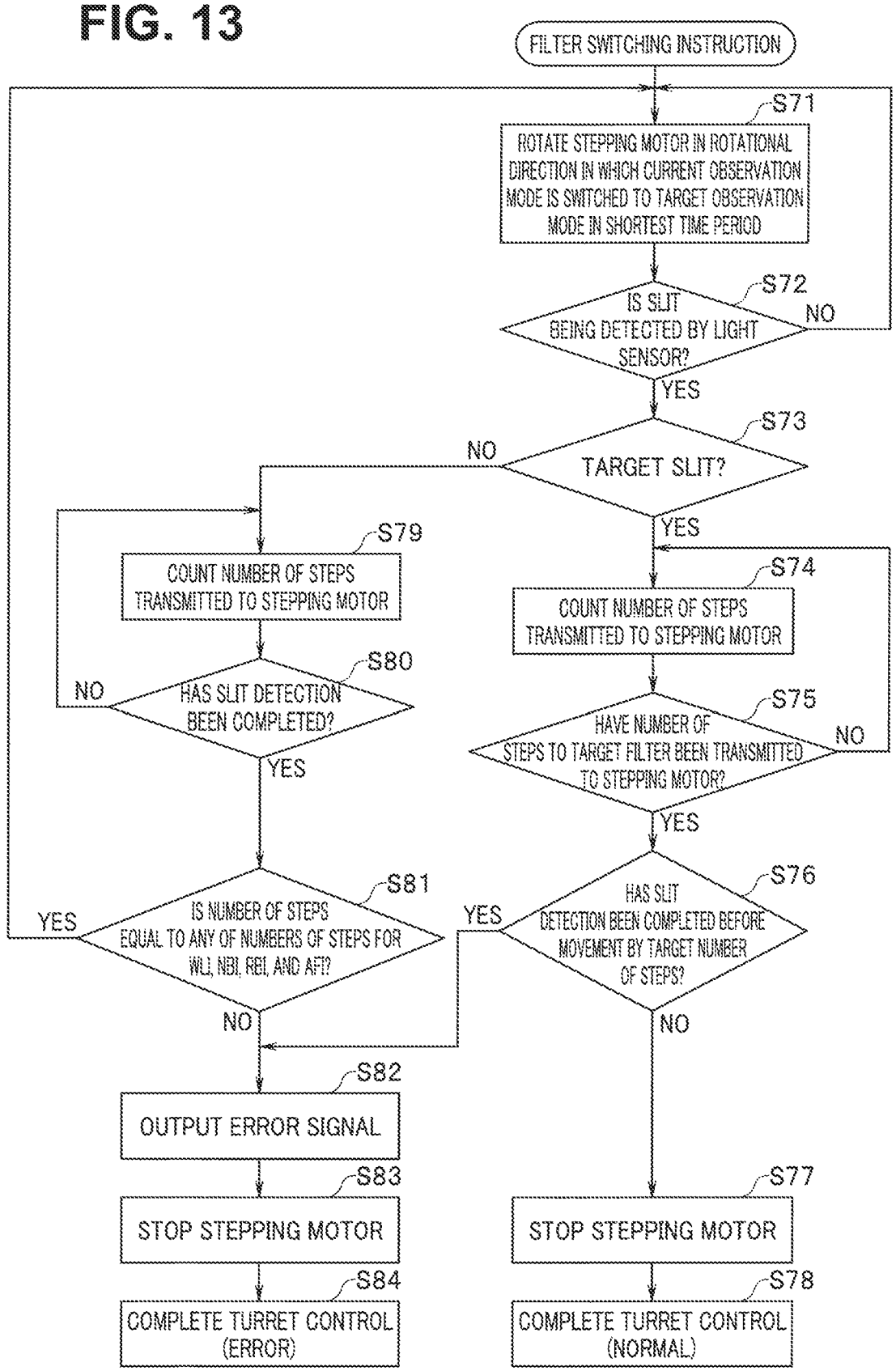
FIG. 13 is a flowchart illustrating a turret control operation in the filter switching device of the second embodiment when filter switching is instructed.
Figure 14:
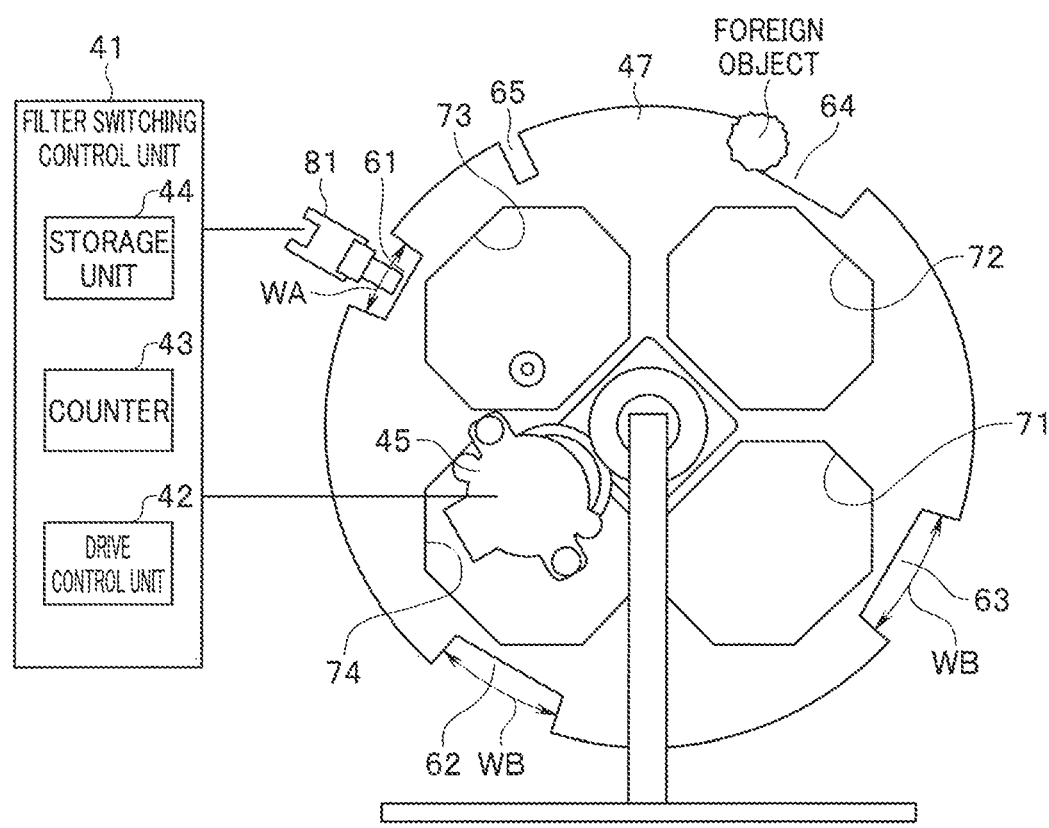
FIG. 14 is a one-side view illustrating the status of the turret in the filter switching device of the second embodiment when a foreign object adheres to a detection target slit.

FIG. 11 is a flowchart illustrating the initial setting operation of the turret in the filter switching device of the second embodiment of the present invention at power-on, and FIG. 12 is a flowchart specifically illustrating the error check subroutine at power-on. FIG. 13 is a flowchart illustrating turret control operation in the filter switching device of the second embodiment when filter switching is instructed. FIG. 14 is a one-side view illustrating the status of the turret in the filter switching device of the second embodiment when a foreign object adheres to a detection target slit.

Effects of Filter Switching Device of Second Embodiment

The following first describes the initial setting operation of the turret in the filter switching device of the second embodiment at power-on.

As illustrated in FIG. 11, the filter switching device of the second embodiment of the present invention executes the error check subroutine before executing the initial setting operation of the turret at power-on (step S50).

FIG. 12 is a flowchart illustrating the error check subroutine. As illustrated in FIG. 12, when the error check subroutine is executed, the drive control unit 42 transmits a predetermined step to the stepping motor 45 for rotational driving so that the turret 47 rotates clockwise in FIG. 2 (step S51).

Similarly to the first embodiment, while controlling the stepping motor 45 to rotate the turret 47, the drive control unit 42 determines whether or not any slit detection signal (the reference position slit detection signal, the first slit detection signal, the second slit detection signal, the third slit detection signal, or the fourth slit detection signal) has been acquired from the photo-interrupter 81 (light sensor) (whether or not any slit has been detected) (step S52).

The photo-interrupter 81 has not detected a slit right after rotation of the turret 47, and thus the drive control unit 42 proceeds to step S57 and determines whether a slit in-detection flag has been set (step S57). The drive control unit 42 continues rotation of the turret 47 until the flag is set.

When the photo-interrupter 81 has detected any slit at the above-described step S52, the drive control unit 42 sets the slit in-detection flag (step S53), and subsequently determines whether the detection flag of the reference position detection slit 65 has been set (step S54). In other words, the drive control unit 42 determines whether the reference position detection slit 65 has passed by the photo-interrupter 81.

When the flag has not been set at step S54, the drive control unit 42 proceeds to step S62, activates the counter 43 to start counting the number of steps transmitted to the stepping motor 45 (step S62), and continues further rotation of the turret 47.

Thereafter, the drive control unit 42 continues monitoring a detection signal from the photo-interrupter 81 and continues further rotation of the turret 47 until acquisition of the detection signal of the slit from the photo-interrupter 81 ends. Note that the counter 43 continues counting in this case.

When having received a notification that acquisition of the detection signal of the slit from the photo-interrupter 81 has ended during monitoring of the detection signal from the photo-interrupter 81 (step S52), at step S57, the drive control unit 42 determines again whether the slit in-detection flag has been set (step S57).

When the slit in-detection flag has been set, the drive control unit 42 compares the number of steps counted by the counter 43 and the number of steps corresponding to the slit width of the reference position detection slit 65 (step S58).

At step S58, when the counted number of steps is equal to the number of steps corresponding to the slit width of the reference position detection slit 65 (in the present embodiment, 10 [step] as described above), the drive control unit 42 determines that the reference position detection slit 65 has passed by the photo-interrupter 81, and sets the detection flag of the reference position detection slit 65 (step S59).

Thereafter, the drive control unit 42 temporarily resets counting by the counter 43 (step S60), and controls the stepping motor 45 to continue rotation of the turret 47 again (step S51).

When the comparison between the number of steps counted by the counter 43 and the number of steps corresponding to the slit width of the reference position detection slit 65 indicates that the numbers of steps are not equal to each other at step S58 described above, in other words, in a state in which the slit in-detection flag has been set (No at step S58), the drive control unit 42 subsequently compares the number of steps counted by the counter 43 with the number of steps for the slit width of the first slit 61, the second slit 62, the third slit 63, or the fourth slit 64 (step S61).

When the number of steps counted by the counter 43 is not equal to the number of steps for the slit width of any slit (the first slit 61, the second slit 62, the third slit 63, or the fourth slit 64) at step S61, it is thought that anomaly has occurred to the turret 47.

For example, when a foreign object such as waste adheres to the slit of the detection target shape portion as illustrated in FIG. 14, the width of the slit is detected to lower than expected, and in this case, the number of steps counted by the counter 43 is measured as a value smaller than the width of any of the above-described slits.

In the present embodiment, an error signal is outputted when such a foreign object such as waste adheres to the slit of the detection target shape portion.

Specifically, in the flowchart of FIG. 12, when the number of steps counted by the counter 43 is not equal to the number of steps of the slit width of any slit (the reference position detection slit 65, the first slit 61, the second slit 62, the third slit 63, or the fourth slit 64) at steps S58 and S61, the drive control unit 42 proceeds to step S63 to output a predetermined error signal, stops the stepping motor 45 (step S64), and completes control of the turret 47 (step S65).

When the reference position detection slit 65 has no anomaly and the drive control unit 42 determines that the reference position detection slit 65 has normally passed by the photo-interrupter 81 at step S58, the drive control unit 42 sets the detection flag of the reference position detection slit 65 (step S59), temporarily resets counting by the counter 43 (step S60), and then controls the stepping motor 45 to continue rotation of the turret 47 again (step S51) as described above.

Thereafter, when having acquired the next slit detection signal from the photo-interrupter 81 (step S52), the drive control unit 42 sets the slit in-detection flag again (step S53) and determines whether the detection flag of the reference position detection slit 65 has been set (step S54).

Since the detection flag of the reference position detection slit 65 has been set at step S59 described above, the drive control unit 42 proceeds from the present step S54 to step S55.

Since the slit detected by the photo-interrupter 81 is a slit other than the reference position detection slit 65 in this case, at step S55, the drive control unit 42 activates the counter 43 again to start counting the number of steps to be transmitted to the stepping motor 45 (step S55).

Thereafter, the drive control unit 42 performs slit detection of the slits (the first slit 61, the second slit 62, the third slit 63, and the fourth slit 64) other than the reference position detection slit 65 (step S56), and returns to the normal initial setting operation when the slits have no anomaly (step S50).

When slit detection of a slit (the first slit 61, the second slit 62, the third slit 63, or the fourth slit 64) other than the reference position detection slit 65 has ended at a stage where a predetermined slit width is not reached (step S52), the drive control unit 42 proceeds to step S57 to check the slit in-detection flag, and then proceeds to step S61 through step S58.

At step S61, the drive control unit 42 compares the number of steps counted by the counter 43 with the number of steps for the slit width of the first slit 61, the second slit 62, the third slit 63, or the fourth slit 64 (step S61).

When the number of steps counted by the counter 43 is not equal to the number of steps for the slit width of any slit (the first slit 61, the second slit 62, the third slit 63, or the fourth slit 64) at step S61, it is thought that anomaly has occurred to the turret 47, and the drive control unit 42 proceeds to step S63 to output a predetermined error signal, stops the stepping motor 45 (step S64), and completes control of the turret 47 (step S65).

In this manner, since the error check subroutine is executed in the initial setting operation of the turret 47 in the second embodiment, error processing can be performed when anomaly has been occurred due to a foreign object such as waste adhering to any slit (the reference position detection slit 65, the first slit 61, the second slit 62, the third slit 63, or the fourth slit 64) as the detection target shape portion.

<Operation when Filter Switching is Instructed by User>

The following describes operation in the filter switching device of the second embodiment when filter switching is instructed by a user.

FIG. 13 is a flowchart illustrating the turret control operation in the filter switching device of the second embodiment when filter switching is instructed.

In the second embodiment as well, similarly to the first embodiment, when observation modes are switched by the observation mode switching operation means not illustrated, the drive control unit 42 receives an optical filter switching instruction through the processor control unit 31 of the video processor 3 or the like.

In the present embodiment, similarly to the first embodiment, the storage unit 44 stores various kinds of information of each slit, for example, information of the slit width of the slit and also stores relative position information (for example, the number of steps) of any other slit (the second slit 62, the third slit 63, or the fourth slit 64) with respect to the first slit 61 (WLI slit) in association with the width dimension of the slit.

Specifically, the storage unit 44 stores the distance from the stop position of the first slit 61 to the stop position of the second slit 62, the third slit 63, or the fourth slit 64 as the rotation angle ([deg]) of the turret 47 and the number of steps of the stepping motor 45. The storage unit 44 stores the rotation angle ([deg]) of the turret 47 and the number of steps of the stepping motor 45 in association with information of the width dimension of each slit.

Similarly to the first embodiment, when having received an instruction to switch the turret 47 to a targeted stop position, the drive control unit 42 controls, based on the relative position information stored in the storage unit 44, the stepping motor 45 to rotate the turret 47 so that the turret 47 reaches the targeted stop position from the current position by a smallest rotational amount.

Specifically, assume that the turret 47 is currently stopping at the above-described initial position. In this case, in the second embodiment as well, the first optical filter 71A (WLI filter 71A) is positioned on the optical path of illumination light emitted from the light source 46, and the first slit 61 corresponding to the first optical filter 71A is stopping while the position of detection by the photo-interrupter 81 is substantially at the center of the slit width.

Then, for example, the NBI observation mode is selected as the observation mode while the turret 47 is stopping at the initial position. In this case, the drive control unit 42 receives, from the processor control unit 31, an instruction to switch the WLI observation mode to the NBI observation mode, in other words, an instruction to switch the optical filter placed on the illumination light optical path from the first optical filter 71A (WLI filter 71A) to the second optical filter 72A (NBI filter 72A).

Having received the instruction, the drive control unit 42 controls rotation of the stepping motor 45 so that the first optical filter 71A corresponding to the current observation mode (in this example, the WLI observation mode) is switched to the second optical filter 72A corresponding to a target observation mode (in this example, the NBI observation mode) by a smallest rotational amount (in a shortest time period) in the turret 47 (step S71). The drive control unit 42 determines whether a slit is being detected by the photo-interrupter 81 (light sensor) (step S72). When a slit is not being detected, the drive control unit 42 returns to step S71. When a slit is being detected, the drive control unit 42 proceeds to step S73.

In this case, the drive control unit 42 acquires relative position information on the stop position of the first slit 61 (corresponding to the first optical filter 71A) and the stop position of the second slit 62 (second optical filter 72A), which is stored in the storage unit 44, derives, based on the information, the rotational direction of the turret 47 and the number of steps of the stepping motor 45 with which the second slit 62 is reached by a smallest rotational amount, and controls rotation of the turret 47 in accordance with the derived rotational direction and the derived number of steps.

The drive control unit 42 rotates the turret 47 in the rotational direction by the number of steps necessary for reaching the second slit 62 corresponding to the target filter (the second optical filter 72A) by the smallest rotational amount.

Thereafter, in the second embodiment, when the photo-interrupter 81 has detected the target second slit 62 (step S73), the drive control unit 42 activates the counter 43 again to start counting the number of steps to be transmitted to the stepping motor 45 (step S74).

Thereafter, the drive control unit 42 transmits, to the stepping motor 45, the number of steps in accordance with the stop position of the second slit 62 corresponding to the target filter (second optical filter 72A) (the number of steps until the position corresponding to the detection signal outputted from the photo-interrupter 81 substantially reaches the center of the slit since the photo-interrupter 81 has detected the edge of the second slit 62) (step S75).

Specifically, in the second embodiment as well, the second slit 62 (NBI slit) has a step width of 25 [deg] and 50 [step], and thus the number of steps for stopping the second slit 62 at a predetermined stop position is 25 [step], which is half of the step width. Accordingly, in this case, the drive control unit 42 transmits the number of steps, 25 [step], to the stepping motor 45 in the second embodiment as well.

In the second embodiment, the drive control unit 42 determines whether detection of the second slit 62 has been completed before the number of counts by the counter 43 reaches the number of steps (25 [step]) (step S76).

When the number of counts by the counter 43 has normally reached the number of steps (25 [step]), the drive control unit 42 stops the stepping motor 45 (step S77) and normally completes optical filter switching (step S78).

When detection of the second slit 62 has been completed before the number of counts by the counter 43 reaches the number of steps (25 [step]) at step S76, it is thought that a foreign object such as waste adheres to the second slit 62, and the drive control unit 42 proceeds to step S82 to output a predetermined error signal, stops the stepping motor 45 (step S83), and completes control of the turret 47 (step S84).

In the second embodiment, at step S73 described above, when the photo-interrupter 81 has not detected the target second slit 62 (step S73), the drive control unit 42 activates the counter 43 to start counting the number of steps to be transmitted to the stepping motor 45 (step S79) and monitors complete of detection of the second slit 62 (step S80).

When detection of the second slit 62 being monitored by the drive control unit 42 has been completed, the drive control unit 42 compares the number of steps counted by the counter 43 with the number of steps for the slit width of the first slit 61, the second slit 62, the third slit 63, or the fourth slit 64 again (step S81).

When the number of steps counted by the counter 43 is not equal to the number of steps for the slit width of any slit (the first slit 61, the second slit 62, the third slit 63, or the fourth slit 64) at step S81, it is thought that anomaly has occurred to the turret 47, and as described above, the drive control unit 42 proceeds to step S82 to output a predetermined error signal, stops the stepping motor 45 (step S83), and completes control of the turret 47 (step S84).

In this manner, in the second embodiment, anomaly of a slit (the reference position detection slit 65, the first slit 61, the second slit 62, the third slit 63, or the fourth slit 64) as the detection target shape portion can be accurately detected and error processing can be performed in the optical filter switching operation as well.

As described above, effective error processing can be performed in the second embodiment, but error processing described below may be executed as a modification of the second embodiment.

<Modification 1>

In Modification 1, error processing is performed, for example, when the stepping motor 45 has failed or the stepping motor 45 has come off the turret 47.

Specifically, in a case of the initial position detection or observation mode switching described above, an error signal is outputted when none of the slits (the reference position detection slit 65 as well as the first slit 61, the second slit 62, the third slit 63, and the fourth slit 64) are detected while rotation of the turret 47 is instructed by the filter switching control unit 41.

For example, when the user performs a predetermined input operation for observation mode switching, the filter switching control unit 41 controls the stepping motor 45 to rotationally drive the turret 47 so that the optical filter corresponding to a desired observation mode reaches a predetermined position. In this case, the stepping motor 45 rotates the turret 47 under control of the filter switching control unit 41.

The photo-interrupter 81 detects whether the filter corresponding to the desired observation mode has reached the predetermined position in the turret 47 based on the existence of a slit or the like.

In this case, when the counter 43, which counts the number of steps of the stepping motor 45, has counted the number of steps until the filter corresponding to the desired observation mode reaches the predetermined position from the current position, the number of steps being stored in the storage unit 44, but has detected no slit, it is determined that there is anomaly such as connection anomaly between the turret 47 and the stepping motor 45 or failure of the stepping motor 45, and an error signal is outputted.

When no slit has been detected after elapse of a predetermined time period while rotation of the stepping motor 45 is instructed by the filter switching control unit 41, it is determined that there is anomaly such as connection anomaly between the turret 47 and the stepping motor 45 or failure of the stepping motor 45, and an error signal is outputted as described above.

The predetermined time period is set to be a time period, for example, five seconds approximately, which is slightly longer than a time period in which the photo-interrupter 81 detects a slit in a normal case.

Accordingly, anomaly such as failure of the stepping motor 45 or cancellation of fixation of the turret 47 and the stepping motor 45 can be detected.

<Modification 2>

Subsequently, Modification 2 will be described below.

In Modification 2, error processing is performed, for example, when no illumination light is emitted because the turret 47 stops at an anomalous position.

Specifically, in a case of the initial position detection, the observation mode switching, or the like, an error signal is outputted when the stepping motor 45 has stopped or when the detection unit has detected no slit after elapse of a predetermined time period while optical filter switching is instructed by the filter switching control unit 41.

In Modification 2, the photo-interrupter 81 always detects a slit when an optical filter is positioned on the illumination light optical path.

With this configuration, it is thought that no optical filter is positioned on the illumination light optical path when no slit has been detected by the photo-interrupter 81 while the stepping motor 45 is stopping, or when no slit has been detected after elapse of a predetermined time period since the filter switching control unit 41 has instructed optical filter switching.

For example, a base metal part of the turret 47 between optical filters is potentially positioned on the illumination light optical path. In this case, illumination light is mostly shielded by base metal of the turret 47 and not inputted to the light guide mounted on the endoscope, and accordingly, almost no illumination light is potentially emitted from a distal end of the endoscope.

In such a case, according to Modification 2, it is determined that the position of the turret 47 is anomalous, and an error signal is outputted.

Third Embodiment

Subsequently, a third embodiment of the present invention will be described below.

A filter switching device of the third embodiment has a main configuration same as the configuration of the first embodiment but is characterized in a configuration in which the first slit (WLI slit) corresponding to the first optical filter (WLI filter) also plays the role of the reference position detection slit 65 in the first embodiment. Other configurations and effects are same as the configurations and effects of the first embodiment, and thus only difference from the first embodiment will be described below, and any common part will not be described.

Figure 15:
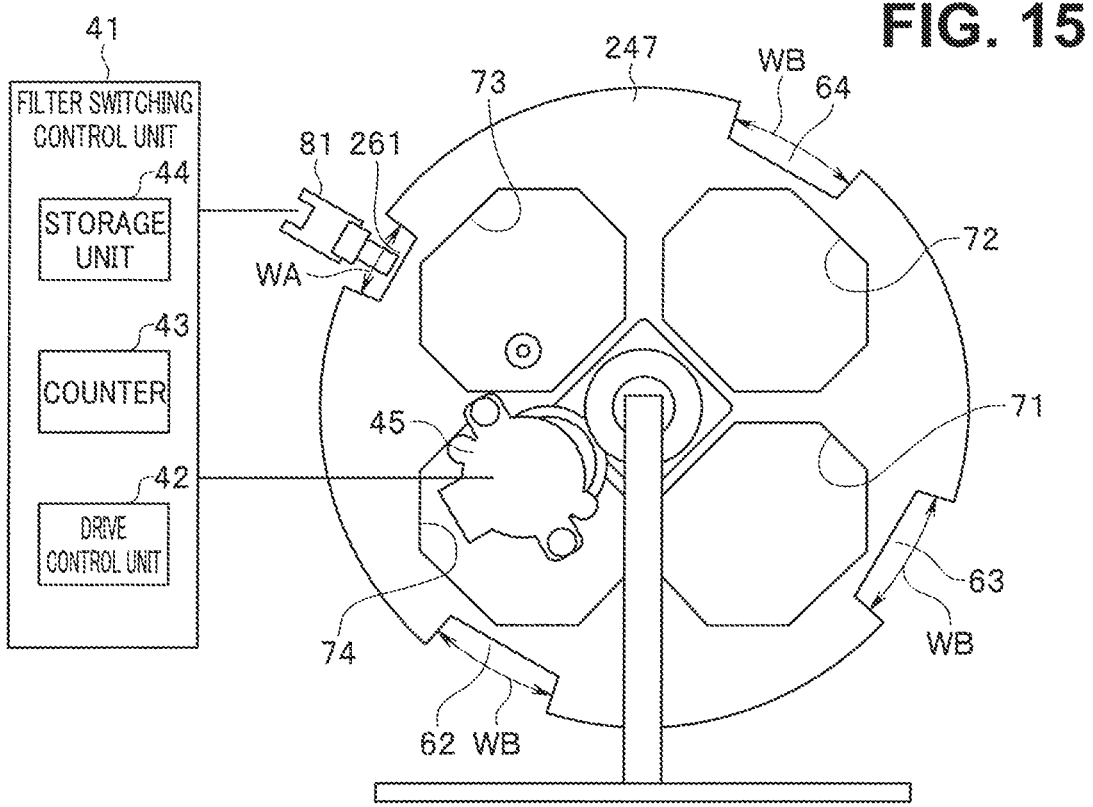
FIG. 15 is a one-side view illustrating one side surface of a filter switching device of a third embodiment of the present invention together with the configuration of the control unit.
Figure 16:
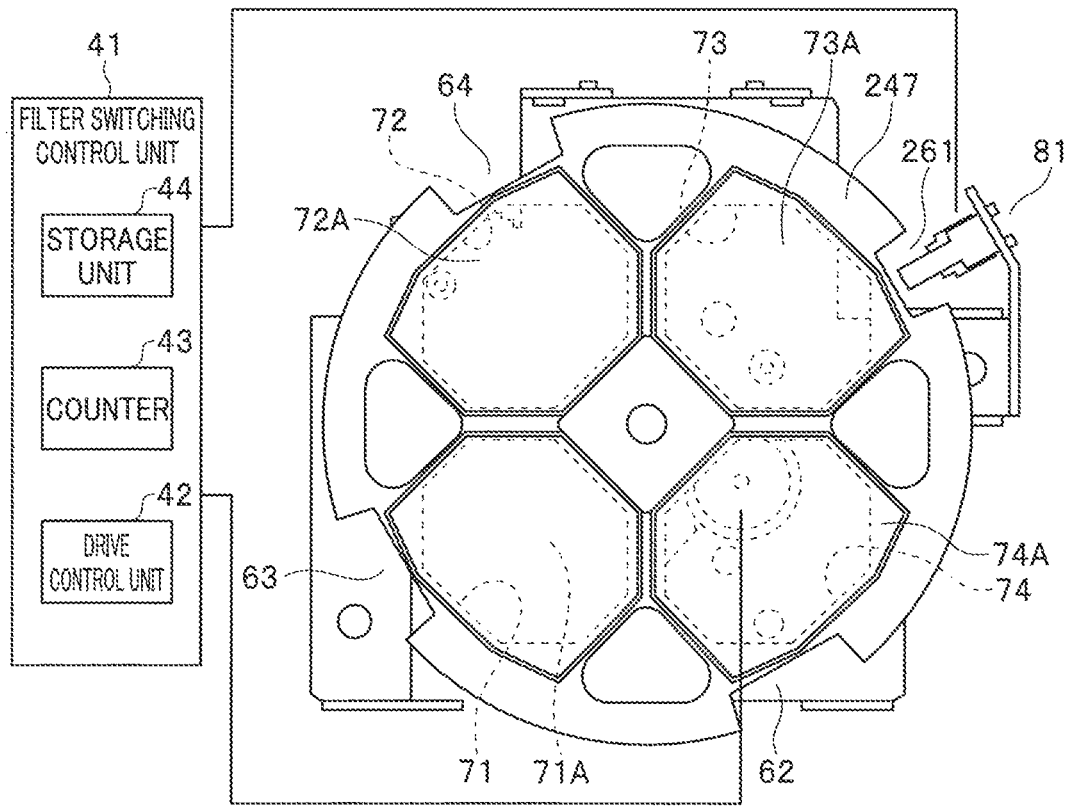
FIG. 16 is a the-other-side view illustrating the other side surface of the filter switching device of the third embodiment together with the configuration of the control unit.

FIG. 15 is a one-side view illustrating one side surface of the filter switching device of the third embodiment of the present invention together with the configuration of the control unit, and FIG. 16 is a the-other-side view illustrating the other side surface of the filter switching device of the third embodiment together with the configuration of the control unit.

In the filter switching device of the third embodiment, a first slit 261 as a first detection target shape portion also functions as the reference position detection slit 65 for detecting a predetermined reference position on the turret 47.

In the third embodiment, when the turret 47 rotates, the photo-interrupter 81 outputs a signal equivalent to the reference detection signal in the first embodiment in response to detection of the first slit 261.

Then, in response to acquisition of the reference detection signal from the photo-interrupter 81, the filter switching control unit 41 controls a stepping pulse (drive signal) to be transmitted to the stepping motor 45. Specifically, the drive control unit 42 of the filter switching control unit 41 controls the stepping motor 45 to stop the turret 47 at a predetermined stop position corresponding to the first slit 261.

In the third embodiment, the first slit 261, the second slit 62, the third slit 63, and the fourth slit 64 are formed so that the slits have predetermined width dimensions, respectively, in the circumferential direction on the predetermined radius centered at the rotational axis of the turret 47.

Specifically in the third embodiment, when the angle of the turret 47 in the circumferential direction is represented by [deg] and the number of steps of the stepping motor is represented by [step], the first slit 261, which also functions as the reference position detection slit, the second slit 62, the third slit 63, and the fourth slit 64 each have the following width dimensions.

The first slit 261: WA (15 [deg](30 [step]))
The second slit 62: WB (25 [deg](50 [step]))
The third slit 63: WB (25 [deg](50 [step]))
The fourth slit 64: WbB (25 [deg](50 [step]))

In the third embodiment, similarly to the first embodiment, the drive control unit 42 monitors a detection signal from the photo-interrupter 81 and continues further rotation of the turret 47 until acquisition of the detection signal of the slit from the photo-interrupter 81 ends. Note that the counter 43 continues counting in this case.

When having received a notification that acquisition of the detection signal of the slit from the photo-interrupter 81 has ended during monitoring of the detection signal from the photo-interrupter 81, the drive control unit 42 compares the number of steps counted by the counter 43 with the number of steps for the slit width of the first slit 261 functioning as the reference position detection slit.

When the counted number of steps is equal to the number of steps (in the present embodiment, 15 [step] as described above) for the slit width of the first slit 261, the drive control unit 42 determines that the first slit 261 has passed by the photo-interrupter 81.

Thereafter, when the photo-interrupter 81 detects the first slit 261 again after having recognized that the first slit 261 has passed, the drive control unit 42 transmits, to the stepping motor 45 based on slit width information of the first slit 261 (WLI slit) stored in the storage unit 44, the number of steps for stopping the first slit 261 (WLI slit) at a predetermined stop position (the number of steps until the position corresponding to the detection signal outputted from the photo-interrupter 81 substantially reaches the center of the slit since the photo-interrupter 81 has detected an edge of the first slit 261).

Note that, in the third embodiment as well, the first slit 261 (WLI slit) is set to have a step width of 15 [deg] and 30 [step], and thus the number of steps for stopping the first slit 261 at the predetermined stop position is 15 [step], which is half of the step width. Accordingly, the drive control unit 42 transmits the number of steps, 15 [step], to the stepping motor 45 in the present embodiment as well.

Thereafter, the drive control unit 42 stops the stepping motor 45 after having transmitted the number of steps (15 [step]) to the stepping motor 45. In this case, the first optical filter 71A (WLI filter 71A) corresponding to the first slit 261 (WLI slit) stops at a position on the optical path of illumination light emitted from the light source 46. Accordingly, control of the initial operation of the turret 47 is completed As described above, according to the filter switching device of the third embodiment, the position of an optical filter on the turret can be recognized with a smaller detection target shape portion, and the optical filter can be accurately placed at a desired position in a short time period.

Note that the present embodiment describes above an example in which, after passing of the first slit 261 is checked, rotation is continued in the same direction until the edge of the first slit 261 is detected again, but the present invention is not limited to this configuration. It is preferable that after passing of the first slit 261 is checked, rotation is performed in the opposite direction and the stepping motor is stopped after 15 [step], which is a predetermined number of steps, is transmitted since the edge of the first slit 261 is detected again, thereby achieving accurate stopping at a desired position in a short time period. With this configuration, it is possible to reach the desired position by a smaller rotation angle.

Fourth Embodiment

Subsequently, a fourth embodiment of the present invention will be described below.

A filter switching device of the fourth embodiment has a main configuration same as the configuration of the first embodiment but is characterized in a plurality of slits corresponding to the reference position detection slit 65 in the first embodiment. Other configurations and effects are same as the configurations and effects of the first embodiment, and thus only difference from the first embodiment will be described below, and any common part will not be described.

Figure 17:
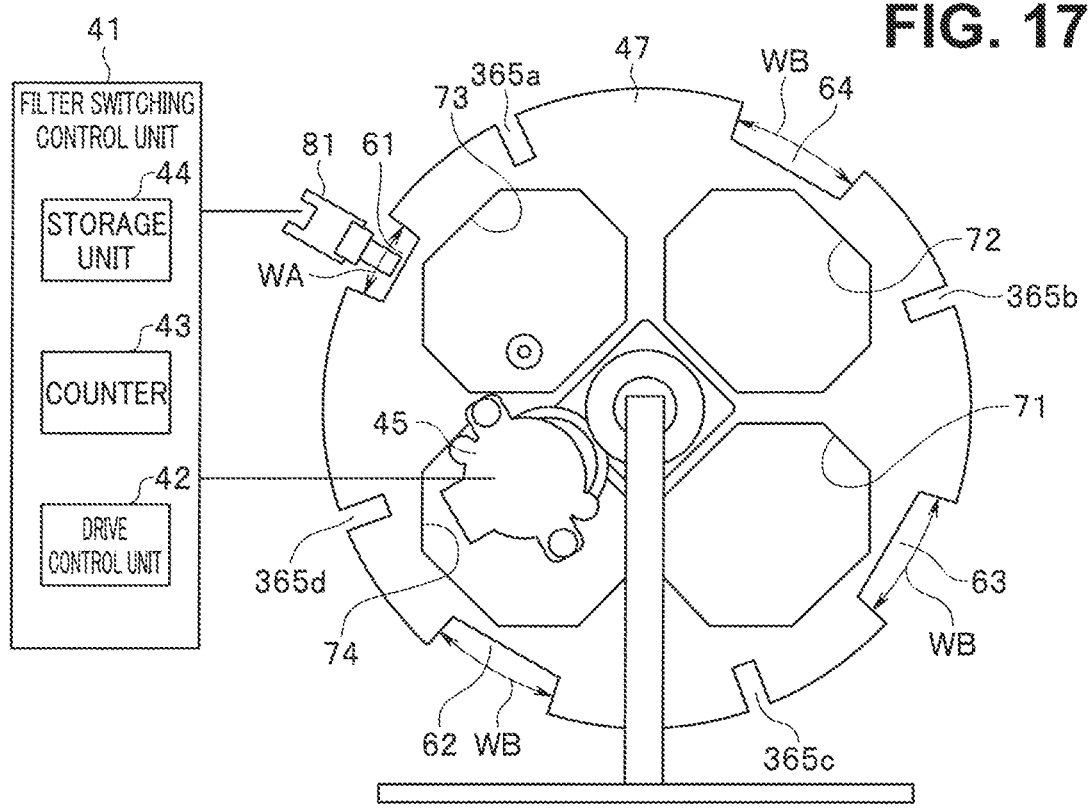
FIG. 17 is a one-side view illustrating one side surface of a filter switching device of a fourth embodiment of the present invention together with the configuration of the control unit.
Figure 18:
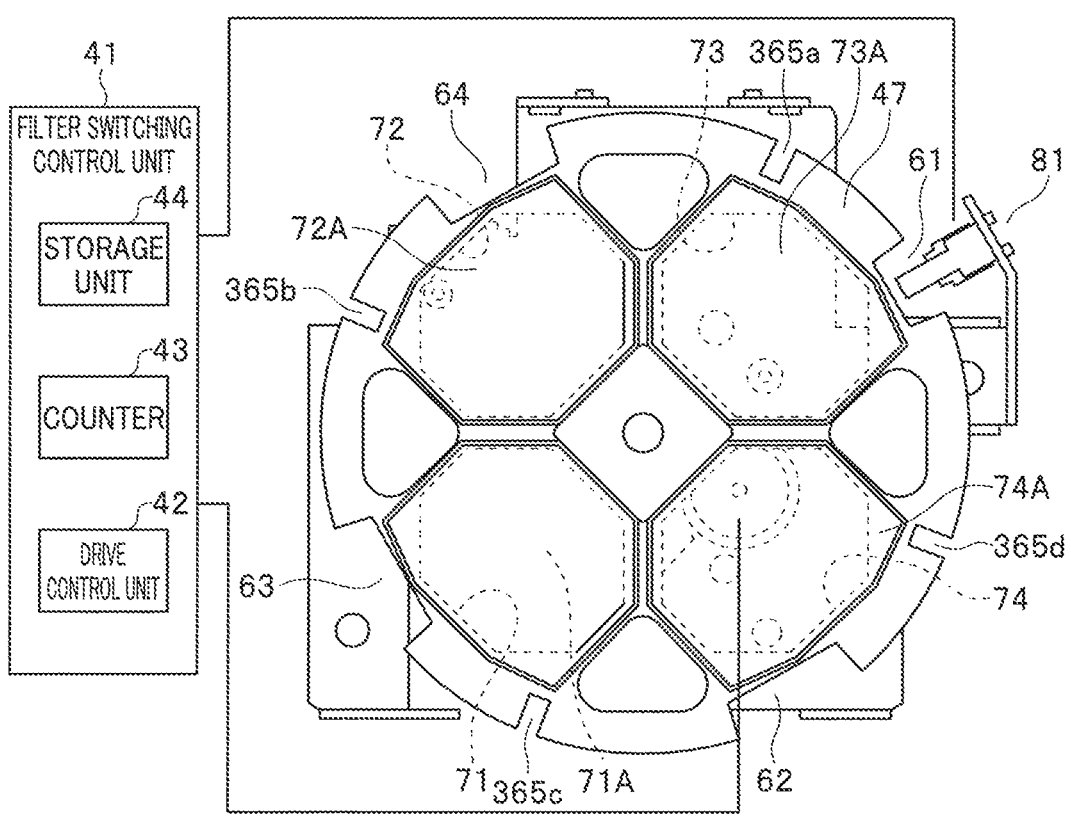
FIG. 18 is a the-other-side view illustrating the other side surface of the filter switching device of the fourth embodiment together with the configuration of the control unit.

FIG. 17 is a one-side view illustrating one side surface of the filter switching device of the fourth embodiment of the present invention together with the configuration of the control unit, and FIG. 18 is a the-other-side view illustrating the other side surface of the filter switching device of the fourth embodiment together with the configuration of the control unit.

As illustrated in FIGS. 17 and 18, in the filter switching device of the fourth embodiment, the turret 47 includes four reference position detection slits 365*a*, 365*b*, 365*c*, and 365*d* formed as reference position detection slits that play a role corresponding to the reference position detection slit 65 in the first embodiment.

The four reference position detection slits 365*a*, 365*b*, 365*c*, and 365*d* are set to have slit widths slightly different from one another so that the types of the slits can be recognized by the photo-interrupter 81.

The four reference position detection slits 365*a*, 365*b*, 365*c*, and 365*d* are controlled by the photo-interrupter 81 and the filter switching control unit 41 and each configured to play a role equivalent to the reference position detection slit 65 in the first embodiment.

Accordingly, finer optical filter switching control can be achieved in the fourth embodiment.

Note that each embodiment is described above with an example in which relative position information of the first to fourth slits and the reference position detection slit is the number of steps between adjacent slits, but the present invention is not limited to this configuration. For example, the order of the first to fourth slits and the reference position detection slit in the circumferential direction may be stored. In this manner, with reduced use of memory capacity, it is possible to derive the number of slits passed before a target slit is reached, and a rotational direction for efficient movement based on this number.

Note that the present invention is not limited to the above-described embodiments but includes various kinds of changes, modifications, and the like without changing the gist of the present invention. For example, the above description is mainly made on a case in which the present invention is an endoscope illumination light switching device, but the present invention is not limited to the case. The present invention may be, for example, an endoscope illumination light switching method that performs operation same as operation of the endoscope illumination light switching device, a computer program for causing a computer to perform processing same as processing of the endoscope illumination light switching device, or a non-temporary storage medium that is readable by a computer storing the computer program.

What is claimed is:

1. A light source device for use with an endoscope, the light source device comprising:
   a rotation body held to be rotatable about a rotational axis, the rotation body comprising:
      at least a first hole and a second hole offset from the first hole in a circumferential direction relative to the rotational axis;
      a first groove recessed from an outer surface of the rotation body toward the rotation axis, the first groove is formed in a first portion of the rotating body corresponding to the first hole;
      a second groove recessed from the outer surface of the rotation body toward the rotation axis;
   an actuator configured to rotate the rotation body;
   a sensor configured to output detection signals in response to detection of the first groove and the second groove; and
   a processor comprising hardware, the processor being configured to control the actuator based on the detection signals to stop the rotation body;
   wherein the second groove is a reference groove positioned at a reference position of the rotation body,
   the sensor is configured to output a reference detection signal in response to detection of the reference groove, and
   the processor is configured to control the actuator to stop the rotation body at a stop position of the first groove in response to a first detection signal detecting the first groove, the first detection signal being acquired after the reference detection signal is acquired from the sensor.

2. The light source device according to claim 1, wherein the rotation body includes a third groove recessed from the outer surface of the rotation body toward the rotation axis, the third groove is formed in a second portion of the rotating body corresponding to the second hole,
   the sensor is configured to output a second detection signal in response to detection of the third groove, and
   after the processor receives a signal from the sensor for switching a position of the rotation body to a targeted position, the processor is configured to:
      where a first circumferential length of the rotation body from the stop position of the first groove to the targeted position in a first rotational direction is shorter than a second circumferential length of the rotation body from the stop position of the first groove to the targeted position in a second rotational direction opposite to the first rotational direction, control the actuator to rotate the rotation body in the first rotational direction.

3. The light source device according to claim 2, further comprising a memory configured to store position information of the first groove relative to the third groove,
   wherein the processor is configured to select the first rotational direction based on the position information.

4. The light source device according to claim 1, wherein the actuator comprises a stepping motor.

5. The light source device according to claim 1, further comprising a memory storing a width of at least one of the first groove and the reference groove, wherein a comparison between a detection signal related to a width of a groove detected by the sensor and stored information in the memory indicates a difference, the processor is configured to execute an error processing sequence.

6. The light source device according to claim 1, further comprising one of:
   a first optical filter covering the first hole;
   a second optical filter covering the second hole; or
   the first optical filter covering the first hole and the second optical filter covering the second hole.

7. The light source device according to claim 1, wherein the actuator comprises a stepping motor configured to rotate the rotation body by receiving stepping pulses, where the light source device is powered on, the processor, the stepping motor, and the sensor are configured to start operating, the processor is configured to start controlling the stepping pulses applied to the stepping motor at the power-on of the light source device, the stepping motor is configured to rotate the rotation body based on the stepping pulses, and where the first detection signal is acquired after the reference detection signal is acquired from the sensor, the processor is configured to control the actuator to rotate the rotation body at the stop position of the first groove.

8. The light source device according to claim 1, wherein the actuator comprises a stepping motor configured to rotate the rotation body by receiving stepping pulses, and widths of the reference groove and the first groove correspond to at least three steps of the stepping motor.

9. The light source device according to claim 8, wherein the rotation body includes a third groove formed at a second position of the rotating body corresponding to the second hole, and where the stepping pulses are transmitted to stop the rotation body at a stop position of any one of the first groove, the second groove, and the third groove, the processor is configured to transmit, to the stepping motor, the stepping pulses for half of a number of steps corresponding to half of the width of the first groove after acquiring the first detection signal outputted from the sensor of an edge of the first groove.

10. The light source device according to claim 1, wherein the rotation body includes a third groove, and the reference groove, the first groove, and the third groove are each a cutout formed at outer surface of the rotation body along two straight lines extending in a radial direction from a rotation center and an arc on a radius.

11. The light source device according to claim 1, wherein the reference groove is a first reference groove;

the rotation body includes a second reference groove, the second reference groove is recessed from the outer surface of the rotation body toward the rotation axis, a width of the first reference groove is different from a width of a second reference groove, and the light source device further comprises a memory configured to store the width of the first reference groove and the width of the second reference groove.

12. The light source device according to claim 1, wherein the second groove is formed in a second portion of the rotating body corresponding to the second hole, and the sensor is configured to output a second detection signal in response to detection of the second groove.

13. The light source device according to claim 12, wherein the processor receives a signal for switching a position of the rotation body to a targeted position, and the processor is configured to:

where the rotation body has a first length from a current position to the targeted position in a first rotational direction shorter than a second length from the current position to the targeted position in a second rotational direction opposite to the first rotational direction, rotate the rotation body in the first rotational direction.

14. The light source device according to claim 1, wherein at least the first hole and the second hole comprises, at least the first hole, the second hole and a third hole, each offset from each other in the circumferential direction relative to the rotational axis.

15. A light source device for use with an endoscope, the light source device comprising:

a rotation body held to be rotatable about a rotational axis, the rotation body comprising:

at least a first hole and a second hole offset from the first hole in a circumferential direction relative to the rotational axis;

a first groove recessed from an outer surface of the rotation body toward the rotation axis, the first groove is formed in a first portion of the rotating body corresponding to the first hole;

a second groove recessed from the outer surface of the rotation body toward the rotation axis;

an actuator configured to rotate the rotation body;

a sensor configured to output detection signals in response to detection of the first groove and the second groove; and a processor comprising hardware, the processor being configured to control the actuator based on the detection signals to stop the rotation body at a stop position;

wherein the second groove is formed in a second portion of the rotating body corresponding to the second hole, and the sensor is configured to output a second detection signal in response to detection of the second groove;

the processor receives a signal for switching a position of the rotation body to a targeted position, and the processor is configured to, where the rotation body has a first length from a current position to the targeted position in a first rotational direction shorter than a second length from the current position to the targeted position in a second rotational direction opposite to the first rotational direction, rotate the rotation body in the first rotational direction.

16. The light source device according to claim 15, further comprising a memory configured to store position information of the first groove relative to the second groove, wherein the processor is configured to select a rotational direction of the rotation body based on the position information stored in the memory.

17. The light source device according to claim 15, wherein the rotation body further includes a reference groove for detecting a reference position on the rotation body, the light source device further comprises a memory storing a width of at least one of the first groove, the second groove, and the reference groove, and the processor is configured to execute an error processing sequence where a comparison between a detection signal related to a width of a groove detected by the sensor and stored information in the memory indicates a difference.

18. The light source device according to claim 15, wherein the actuator comprises a stepping motor configured to rotate the rotation body, the rotation body further includes a reference groove corresponding to a reference position of the rotation body, and a width of each of the reference groove and the first groove is at least three steps of the stepping motor.

19. The light source device according to claim 18, wherein stepping pulses are transmitted to the stepping motor to stop the rotation body at a stop position of one of the first groove, the second groove, and the reference groove, and the processor is configured to transmit, to the stepping motor, the stepping pulses for half of a number of steps corresponding to half of the width of the one of the first groove, the second groove, and the reference groove from an edge of the one of the first groove, the second groove, and the reference groove.

20. The light source device according to claim 15, wherein
   the first groove comprises a reference groove corresponding to a reference position of the rotation body,
   a width of the first groove is different from a width of the second groove,
   the sensor is configured to output a reference detection signal in response to detection of the first groove, and
   the processor is configured to control the actuator to stop the rotation body at the first groove by controlling a drive signal transmitted to the actuator in response to acquisition of the reference detection signal from the sensor.

* * * * *